United States Patent
Harkness et al.

(10) Patent No.: US 11,819,021 B2
(45) Date of Patent: Nov. 21, 2023

(54) PEPTIDES AND METHODS AND USES THEREOF FOR MODULATING ANAPHASE PROMOTING COMPLEX (APC) ACTIVITY

(71) Applicants: University of Saskatchewan, Saskatoon (CA); NATIONAL RESEARCH COUNCIL OF CANADA, Ottawa (CA)

(72) Inventors: Troy Harkness, Saskatoon (CA); Terra Gayle Arnason, Saskatoon (CA); Pankaj Bhowmik, Saskatoon (CA)

(73) Assignee: University of Saskatchewan & National Research Council of Canada, Saskatoon (CA)

(*) Notice: Subject to any disclaimer, the term of this patent is extended or adjusted under 35 U.S.C. 154(b) by 2 days.

(21) Appl. No.: 16/500,585

(22) PCT Filed: Apr. 4, 2018

(86) PCT No.: PCT/CA2018/050414
§ 371 (c)(1),
(2) Date: Oct. 3, 2019

(87) PCT Pub. No.: WO2018/184107
PCT Pub. Date: Oct. 11, 2018

(65) Prior Publication Data
US 2020/0123558 A1  Apr. 23, 2020

Related U.S. Application Data

(60) Provisional application No. 62/481,215, filed on Apr. 4, 2017.

(51) Int. Cl.
| | |
|---|---|
| *C07K 7/08* | (2006.01) |
| *A01N 37/46* | (2006.01) |
| *C07K 4/00* | (2006.01) |
| *C07K 5/08* | (2006.01) |
| *C07K 5/103* | (2006.01) |
| *C07K 7/06* | (2006.01) |
| *C12N 5/073* | (2010.01) |
| *C12N 15/82* | (2006.01) |
| *A01N 63/50* | (2020.01) |
| *A61P 35/00* | (2006.01) |
| *A61K 8/64* | (2006.01) |

(52) U.S. Cl.
CPC ............ *A01N 37/46* (2013.01); *A01N 63/50* (2020.01); *A61K 8/64* (2013.01); *A61P 35/00* (2018.01); *C07K 4/00* (2013.01); *C07K 5/08* (2013.01); *C07K 5/1005* (2013.01); *C07K 7/06* (2013.01); *C07K 7/08* (2013.01); *C12N 5/0603* (2013.01); *C12N 15/8266* (2013.01); *C12N 15/8267* (2013.01); *C12N 15/8271* (2013.01)

(58) Field of Classification Search
None
See application file for complete search history.

(56) References Cited

U.S. PATENT DOCUMENTS

| | | | |
|---|---|---|---|
| 6,184,205 B1* | 2/2001 | Sparks | C40B 30/04 514/21.4 |
| 2015/0197765 A1 | 7/2015 | Guo et al. | |
| 2017/0322219 A1 | 11/2017 | Wandall et al. | |

OTHER PUBLICATIONS

Kastl et al. Mad2 Inhibitor-1 (M2I-1): a Small Molecule Protein-Protein Interaction Inhibitor Targeting the Mitotic Spindle Assembly Checkpoint. ACS Chemical Biolog. 2015. 10:1661-1666.*
Allen et al. ('Why are a3 ions rarely observed?' J Am Soc Mass Spectrom 2008 v19 pp. 1764-1770). (Year: 2008).*
Panchenko et al. ('Prediction of functional sites by analysis of sequence and structure conservation' Protein Science v13 2004 pp. 884-892) (Year: 2004).*
Pommie et al. ('IMGT standardized criteria for statistical analysis of immunoglobulin V-Region amino acid properties' Journal of Molecular Recognition 2004 v17 pp. 17-32) (Year: 2004).*
NCBI BLAST sequence rvrrlt (retrieved from https://blast.ncbi.nlm.nih.gov/Blast.cgi on Aug. 19, 2021, 19 pages) (Year: 2021).*
NCBI BLAST sequence arvrrlt (retrieved from https://blast.ncbi.nlm.nih.gov/Blast.cgi on Feb. 23, 2022, 27 pages) (Year: 2022).*
Odaert et al. (Nonnative capping structure initiates helix folding in an annexin I fragment A H NMR conformational study Biochemistry v34 1995 pp. 12820-12829) (Year: 1995).*
NCBI BLAST sequence prplppl (retrieved from https://blast.ncbi.nlm.nih.gov/Blast.cgi on Dec. 5, 2022, 32 pages) (Year: 2022).*
Kastl et al., ACS Chemical Biology, 2015, vol. 10, pp. 1661-1666.
Wassmann and Benezra, Proceedings of the National Academy of Science USA, 1998, vol. 95, pp. 11193-11198.
Harkness et al., Genetics, 2004, vol. 168, pp. 759-774.
Harkness, T.A.A., Current Genomics, 2006, vol. 7(4), pp. 263-272.
Malo et al., Aging, Apr. 2016 (Apr. 2016), vol. 8(4), pp. 810-828.
Postnikoff et al., PLoS Genetics, Mar. 2012 (Mar. 2012), vol. 8(3), pp. 1-13.
Wasch and Engelbert, Oncogene, 2005, vol. 24, pp. 1-10.
Uuganbayar et al., Small Peptides Homologous to the Histone Variant Htz1 Extend Yeast Lifespan in an Anaphase Promoting Complex-Dependent Manner, Epigenetics Meeting—Epigenetics Eh!—London, ON, Canada—Jun. 24-27, 2014.
Davies et al. (2017) Metformin inhibits the development, and promotes the resensitization, of treatment-resistant breast cancer. Plos One 12(12): e0187191.
Harkness et al. (2004). A functional analysis reveals dependence on the anaphase-promoting complex for prolonged life span in yeast. Genetics 168:759-74.
Postnikoff and Harkness (2014). Replicative and chronological life-span assays. Methods Mol Biol 1163:223-7.

(Continued)

*Primary Examiner* — Ronald T Niebauer
(74) *Attorney, Agent, or Firm* — Bereskin & Parr LLP/S.E.N.C.R.L., s.r.l.; Ainslie Parsons

(57) ABSTRACT

Novel activators of the APC complex and methods and uses of these activators are provided. In particular, the activators are used for increasing resistance to stress and/or increasing lifespan in a plant or mammalian cell, in a plant or mammalian embryo or in a plant or subject. The activators are also used for treating cancer in a subject.

Figure 1A:
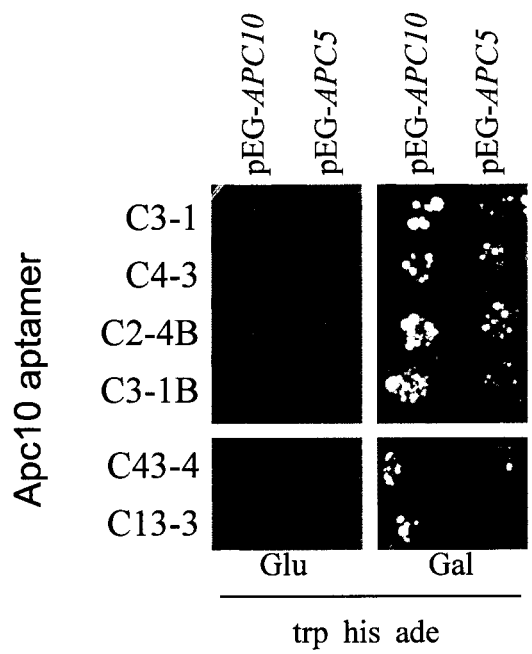

15 Claims, 14 Drawing Sheets
Specification includes a Sequence Listing.

(56) References Cited

OTHER PUBLICATIONS

Postnikoff et al (2012). The yeast forkhead transcription factors fkh1 and fkh2 regulate lifespan and stress response together with the anaphase-promoting complex. PLoS Genet 8:e1002583.
Menzel et al. (2014). The anaphase promoting complex regulates yeast lifespan and rDNA stability by targeting Fob1 for degradation. Genetics 196:693-709.
Harkness el al. (2002). The ubiquitin-dependent targeting pathway in *Saccharomyces* cerevisiae plays a critical role in multiple chromatin assembly regulatory steps. Genetics 162:615-32.
Harkness et al (2005). Contribution of CAF-I to anaphase-promoting-complex-mediated mitotic chromatin assembly in *Saccharomyces* cerevisiae. Eukaryot Cell 4:673-84.
Turner et al. (2010). The *Saccharomyces* cerevisiae anaphase-promoting complex interacts with multiple histone-modifying enzymes to regulate cell cycle progression. Eukaryot Cell 9:1418-31.
Islam et al. (2011). Antagonistic Gcn5-Hda1 interactions revealed by mutations to the Anaphase Promoting Complex in yeast. Cell Div 6:13.
Jiao et al (2015). The SNF1 Kinase Ubiquitin-associated Domain Restrains Its Activation, Activity, and the Yeast Life Span. J Biol Chem 290:15393-404.
Malo et al (2016). Mitotic degradation of yeast Fkh1 by the Anaphase Promoting Complex is required for normal longevity, genomic stability and stress resistance. Aging 8:810-30.
Feser et al. (2010). Elevated histone expression promotes life span extension. Mol Cell 39:724-35.
Yu et al. (2013). Histone variant Htz1 promotes histone H3 acetylation to enhance nucleotide excision repair in Htz1 nucleosomes. Nucleic Acids Res 41:9006-19.
Millar et al. (2006). Acetylation of H2AZ Lys 14 is associated with genome-wide gene activity in yeast. Genes Dev 20:711-22.
Harreman et al. (2009). Distinct ubiquitin ligases act sequentially for RNA polymerase II polyubiquitylation. PNAS 106:20705-10.
Ribar et al. (2007). ELA1 and CUL3 are required along with ELC1 for RNA polymerase II polyubiquitylation and degraciation in DNA-damaged yeast cells. MCB 27:3211-6.
Hanlon et al. (2011). The stress response factors Yap6, Cin5, Phd1, and Skn7 direct targeting of the conserved co-repressor Tup1-Ssn6 in S. cerevisiae. PLoS One 6:e19060.
Furuchi et al. (2001). Two nuclear proteins, Cin5 and Ydr259c, confer resistance to cisplatin in *Saccharomyces* cerevisiae. Mol Pharmacol 59(3):470-4.
Jackson et al. (2000). Novel roles for elongin C in yeast. Biochim Biophys Acta 1491:161-76.
Nevitt et al. (2004). YAP4 gene expression is induced in response to several forms of stress in *Saccaromyces* cerevisiae. Yeast 21:1365-74.
Thornton et al. (2006) An architectural map of the anaphase-promoting complex. Genes Dev 20: 449-460.
Eloy et al. The role of the Anaphase-promoting complex/cyclosome in plant growth. Crit Rev Plant Sci. 2015; 34:487-505.

\* cited by examiner

Fig. 7

```
SEQ ID
NO:
1                              NGSSHNDLRVRRLTLISRLC        C43-4 aptamer!
25    61 TAVLEYLTAEVLELAGNAAKDLKVKRITPRHLQLAIRGDD 100   Sc Htz1!
26    56 AAILEYLTAEVLELAGNASKDLKVKRITPRHLQLAIRGDE  95   Hs H2A.Z!
27    56 AAILEYLTAEVLELAGNASKDLKVKRITPRHLQLAIRGDE  95   Mm H2A.Z!
28    56 AAILEYLTAEVLELAGNASKDLKVKRITPRHLQLAIRGDE  95   Dm H2A var.
```

Fig. 8

```
SEQ ID
NO:
24                            RMPQWWQWMWVRAK              C2-4B aptamer!
30   991 KMILYDLCDNVTTQWREWMFPHNETLPALG 1020   Sc Sum1!
31   121        VLTGKKIPRWSNWCWLFGLLSGLAM  145   Sc Pex11 (perox)!
32   124 FQDLNKWYHEKMPKWSQWVAKGSAAYL      150   Sc Ssh3 (mito)!
33    61        LTEFEKRNPQWWKVTLRSFGGLLIAF  86   Sc Ydl157c (mito)!
                                                                !
```

Fig. 9A
Fig. 9B
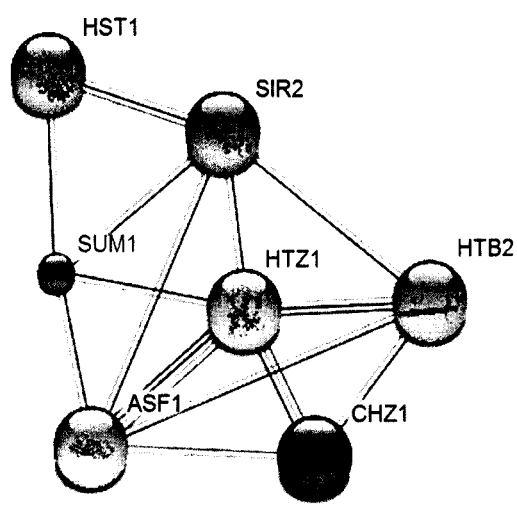
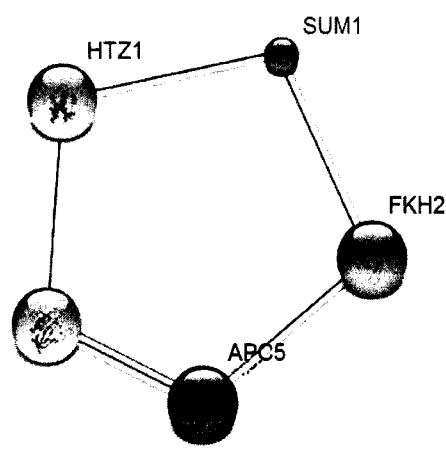

Fig. 13
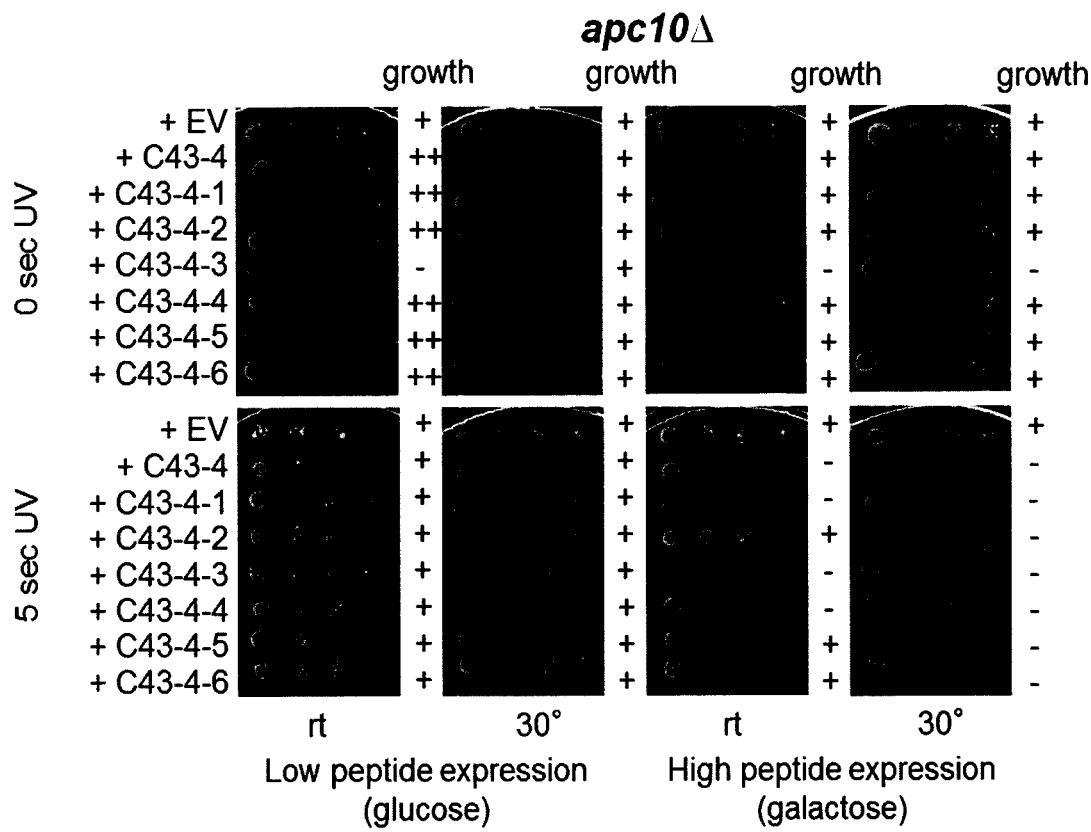
Fig. 14A
Fig. 14B
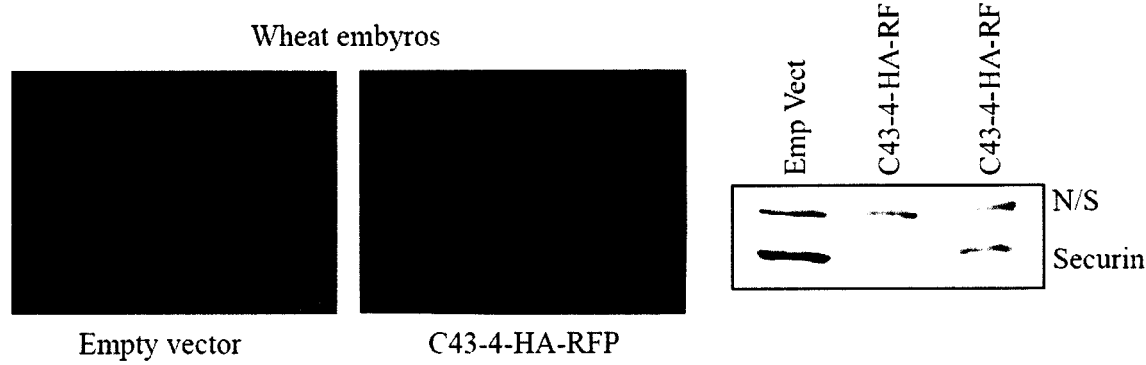

PEPTIDES AND METHODS AND USES THEREOF FOR MODULATING ANAPHASE PROMOTING COMPLEX (APC) ACTIVITY

REFERENCE TO CROSS-RELATED APPLICATION

This application is a national phase entry of PCT/CA2018/050414 filed Apr. 4, 2018 (which designates the U.S.), which claims the benefit of priority to U.S. Provisional Application No. 62/481,215 filed Apr. 4, 2017, the contents of which are incorporated herein by reference in their entirety.

INCORPORATION OF SEQUENCE LISTING

A computer readable form of the Sequence Listing "13764-P52925US02_SequenceListing.txt" (12,888 bytes), submitted via EFS-WEB and amended on May 6, 2020, is herein incorporated by reference.

FIELD

This disclosure relates to novel activators of the Anaphase Promoting Complex (APC) and to methods and uses thereof. In particular, the disclosure relates to methods and uses of the activators for modulating APC activity, increasing resistance to stress and/or increasing lifespan in a plant or mammalian cell, in a plant or mammalian embryo or in a plant or subject. The disclosure also relates to methods and uses of the activators for treating cancer.

BACKGROUND

Evidence is accumulating that cellular lifespan correlates to the damage repair capacity of the cell. Genetic screens in model organisms, from yeast to flies, have demonstrated that genes involved in stress response networks play a decisive role in lifespan determination. Using the brewing yeast model system, it has been shown that regulated cell cycle progression is tightly linked with stress response and normal longevity. Work characterizing the Anaphase Promoting Complex (APC) in yeast, a large highly conserved complex of proteins required for the targeting of substrates for ubiquitin-dependent degradation, has described a number of novel roles and substrates for the APC. The APC is largely known to target proteins that inhibit mitotic progression and G1 maintenance for degradation.

In yeast, the APC has been identified as playing a role in stress response, chromatin assembly regulatory steps, cell cycle progression and longevity (Harkness et al, 2004; Postnikoff et al, 2012; Harkness et al, 2002; Turner et al, 2010).

SUMMARY

Provided herein are activators of the Anaphase Promoting Complex (APC), methods and uses thereof and related reagents.

Accordingly an aspect includes a method for increasing resistance to stress and/or increasing lifespan in a plant, microbial or mammalian cell, in a plant or mammalian embryo or in a plant or subject comprising contacting or introducing into the cell, embryo or plant or introducing or administering to the subject an activator of APC.

Also provided, is use of an activator of the Anaphase Promoting Complex (APC) for increasing resistance to stress and/or increasing lifespan in a plant or mammalian cell, in a plant or mammalian embryo or in a plant or subject.

Further provided is use of an activator of APC for treating cancer in a subject.

In an embodiment, the activator of APC increases APC activity measured by a reduction of APC substrate level of at least 10%, at least 20%, at least 30%, at least 40%, at least 50%, at least 60%, at least 70% or at least 80% compared to a cell, plant, embryo, or cell of a subject not contacted, introduced or administered the activator.

In an embodiment, the activator is a molecule that binds and inhibits activity of Mad2.

In an embodiment, the activator is Mad2 inhibitor-1.

In an embodiment, the activator binds APC and/or increases the viability of an APC mutant compared to an APC mutant not contacted, introduced or administered the activator.

In an embodiment, the activator is a peptide comprising:
amino acid sequence XSSHXDAXXXRXT (SEQ ID NO: 24), wherein X is any amino acid, preferably wherein the amino acid sequence is GSSHNDARVRRLT (SEQ ID NO: 34);
amino acid sequence ETETFHPITRHLIVP (SEQ ID NO: 13) and/or has at least 50, 60, 70, 80, 90, 95 or 99% sequence identity thereto;
amino acid sequence HPRRQPKRPI (SEQ ID NO: 15), amino acid sequence THGGRHP (SEQ ID NO: 16) or amino acid sequence SYNTIKYHETHGGRHPRRQP (SEQ ID NO: 17) and/or has at least 50, 60, 70, 80, 90, 95 or 99% sequence identity to any of the foregoing;
amino acid sequence GALKEVCICIVESVGGEVFSGP (SEQ ID NO: 6) and/or has at least 50, 60, 70, 80, 90, 95 or 99% sequence identity thereto;
amino acid sequence that comprises SKWT (SEQ ID NO: 35) and amino acid sequence MOMS (SEQ ID NO: 36), preferably wherein the peptide comprises SKWTWRMCMS (SEQ ID NO: 37);
amino acid sequence PRP (SEQ ID NO: 38) and amino acid sequence PPL (SEQ ID NO: 39), preferably wherein the peptide comprises PRPWGPPL (SEQ ID NO: 40);
amino acid sequence RRCLSIRTENLAWEGKFLRV (SEQ ID NO: 9) and/or has at least 50, 60, 70, 80, 90, 95 or 99% sequence identity thereto;
amino acid sequence VRQKSDKEYERVLGLGLRRL (SEQ ID NO: 10) or SWLNGSGGVVLWLFSNFCCG (SEQ ID NO: 11) and/or has at least 50, 60, 70, 80, 90, 95 or 99% sequence identity with VRQKSDKEYERVLGLGLRRL (SEQ ID NO: 10) or SWLNGSGGVVLWLFSNFCCG (SEQ ID NO: 11), comprises at least 5, 6, 7 or 8 contiguous amino acids of VRQKSDKEYERVLGLGLRRL (SEQ ID NO: 10) or SWLNGSGGVVLWLFSNFCCG (SEQ ID NO: 11)
amino acid sequence GSSHNDLRVRRLT (SEQ ID NO: 12) or RMPQWWQWMWV (SEQ ID NO: 4) and/or has at least 50, 60, 70, 80, 90, 95 or 99% sequence identity with GSSHNDLRVRRLT (SEQ ID NO: 12) or RMPQWWQWMWV (SEQ ID NO: 4); or
a conservatively substituted variant of any one of (a) to (j) or a part of any one of (a) to (j) comprising at least 5, 6, 7 or 8 contiguous amino acids of any thereof;
and optionally wherein the peptide has a maximum length of 30 amino acids.

In an embodiment, the peptide comprises GSSHNDARVRRLT (SEQ ID NO: 34).

In an embodiment, the peptide comprises or consists of NGSSHNDLRVRRLTLISRLC (SEQ ID NO: 1), NGSSHN- DARVRRLTLISRLC (SEQ ID NO. 2), CECLETETFH-PITRHLIVPV (SEQ ID NO. 3), PSYNTIKYHETHGGRH-PRRQPKRPI (SEQ ID NO: 5), GALKEVCICIVESVGGEVFSGP (SEQ ID NO: 6), SKWTWRMCMSWTVDRFAPVPWP (SEQ ID NO: 7), GRMLMTYLMYFMVLWVPRPWGPPL (SEQ ID NO: 8), RRCLSIRTENLAWEGKFLRV (SEQ ID NO: 9) or a conservatively substituted variant thereof.

In an embodiment, the peptide comprises:
VRQKSDKEYERVLGLGLRRL (SEQ ID NO: 10) or SWLNGSGGVVLWLFSNFCCG (SEQ ID NO: 11) and/or has at least 50, 60, 70, 80, 90, 95 or 99% sequence identity with VRQKSDKEY-ERVLGLGLRRL (SEQ ID NO: 10) or SWLNGSGGVVLWLFSNFCCG (SEQ ID NO: 11), or
comprises at least 5, 6, 7 or 8 contiguous amino acids of VRQKSDKEYERVLGLGLRRL (SEQ ID NO: 10) or SWLNGSGGVVLWLFSNFCCG (SEQ ID NO: 11); and
wherein the peptide increases the viability of an APC5 temperature sensitive mutant, and has a maximum length of 30 amino acids.

In an embodiment, the peptide comprises or consists of VRQKSDKEYERVLGLGLRRL (SEQ ID NO: 10) or SWLNGSGGVVLWLFSNFCCG (SEQ ID NO: 11) or a conservatively substituted variant thereof.

In an embodiment, the activator is or includes a compound comprising the peptide conjugated to an enhancer moiety or a composition comprising the peptide or compound.

In an embodiment, the method or use is for delaying aging, increasing lifespan and/or increasing stress resistance in the cell, embryo, plant or subject.

In an embodiment, the plant cell, embryo or plant is a crop cell, embryo or plant, optionally a wheat cell, embryo or plant.

In an embodiment, the subject is in need thereof.

In an embodiment, the subject is a mammal, preferably a human.

In an embodiment, the method or use is for treating cancer in the subject in need thereof.

In an embodiment, the cancer is breast cancer or lymphocytic cancer.

In an embodiment, the activator is for use with a chemotherapeutic agent.

Also provided are peptide activators of APC.

Accordingly a further aspect is a peptide comprising:
amino acid sequence XSSHXDAXXXRXT (SEQ ID NO: 24), wherein X is any amino acid, preferably wherein the a mino acid sequence is GSSHNDARVRRLT (SEQ ID NO: 34);
amino acid sequence ETETFHPITRHLIVP (SEQ ID NO: 13);
amino acid sequence HPRRQPKRPI (SEQ ID NO: 15), amino acid sequence THGGRHP (SEQ ID NO: 16) or amino acid sequence SYNTIKYHETHGGRHPRRQP (SEQ ID NO: 17);
amino acid sequence GALKEVCICIVESVGGEVFSGP (SEQ ID NO: 6);
amino acid sequence SKWT (SEQ ID NO: 35) and amino acid sequence MOMS (SEQ ID NO: 36), preferably wherein the peptide comprises SKWTWRMCMS (SEQ ID NO: 37);
amino acid sequence PRP (SEQ ID NO: 38) and amino acid sequence PPL (SEQ ID NO: 39), preferably wherein the peptide comprises PRPWGPPL (SEQ ID NO: 40);
amino acid sequence RRCLSIRTENLAWEGKFLRV (SEQ ID NO: 9);
amino acid sequence VRQKSDKEYERVLGLGLRRL (SEQ ID NO: 10) or SWLNGSGGVVLWLFSNFCCG (SEQ ID NO: 11) or has at least 50, 60, 70, 80, 90, 95 or 99% sequence identity with VRQKSDKEY-ERVLGLGLRRL (SEQ ID NO: 10) or SWLNGSGGVVLWLFSNFCCG (SEQ ID NO: 11), or
a conservatively substituted variant of any one of (a) to (h) or a part of any one of (a) to (h) comprising at least 5, 6, 7 or 8 contiguous amino acids of any thereof;
optionally wherein the peptide has a maximum length of 30 amino acids.

In an embodiment, the peptide comprises the amino acid sequence GSSHNDARVRRLT (SEQ ID NO: 24).

In an embodiment, the peptide comprises the amino acid sequence ETETFHPITRHLIVP (SEQ ID NO: 13).

In an embodiment, the peptide comprises the amino acid sequence NGSSHNDARVRRLTLISRLC (SEQ ID NO: 2), CECLETETFHPITRHLIVPV (SEQ ID NO: 3, PSYNTIKY-HETHGGRHPRRQPKRPI (SEQ ID NO: 5), GALKEVCI-CIVESVGGEVFSGP (SEQ ID NO: 6), SKWTWRMCMSWTVDRFAPVPWP (SEQ ID NO: 7), GRMLMTYLMYFMVLWVPRPWGPPL (SEQ ID NO: 8), RRCLSIRTENLAWEGKFLRV (SEQ ID NO: 9) or a conservatively substituted variant thereof.

In an embodiment, the peptide binds increases the viability of a cell with defective APC function and/or binds the APC.

In an embodiment, the peptide:
(a) has at least 50, 60, 70, 80, 90, 95 or 99% sequence identity with VRQKSDKEYERVLGLGLRRL (SEQ ID NO: 10) or SWLNGSGGVVLWLFSNFCCG (SEQ ID NO: 11), or
(b) comprises at least 5, 6, 7 or 8 contiguous amino acids of VRQKSDKEYERVLGLGLRRL (SEQ ID NO: 10) or SWLNGSGGVVLWLFSNFCCG (SEQ ID NO: 11).

The peptide of claim 24, wherein the peptide comprises or consists of VRQKSDKEYERVLGLGLRRL (SEQ ID NO: 10) or SWLNGSGGVVLWLFSNFCCG (SEQ ID NO: 11) or a conservatively substituted variant thereof.

Also provided in another aspect is a compound comprising the peptide described herein and an enhancer moiety.

In an embodiment, the enhancer moiety is a permeability enhancer, stability enhancer or bioavailability enhancer.

Another aspect is a nucleic acid encoding a peptide described herein.

A further aspect is directed to a vector comprising the nucleic acid described herein.

Yet a further aspect is a composition comprising the peptide, nucleic acid, vector or compound and a carrier.

Also provided in another aspect is a recombinant plant, microbial or mammalian cell, plant or mammalian embryo, plant or mammal that expresses:
a peptide wherein the peptide comprises
a peptide described herein;
GSSHNDLRVRRLT (SEQ ID NO: 12) or RMPQWWQWMWV (SEQ ID NO: 4) or peptide that has at least 50, 60, 70, 80, 90, 95 or 99% sequence identity with GSSHNDLRVRRLT (SEQ ID NO: 12 or RMPQWWQWMWV(SEQ ID NO: 4) or part that comprises at least 5, 6, 7 or 8 contiguous amino acids of GSSHNDLRVRRLT (SEQ ID NO: 12) or RMPQWWQWMWV (SEQ ID NO: 4), optionally wherein the peptide has a maximum length of 30 amino acids;

a compound described herein wherein the enhancer moiety is a carrier protein,
a nucleic acid described herein; or
a vector described herein.

In an embodiment, the cell, plan or embryo is a recombinant plant cell, plant embryo or plant optionally wherein the plant, plant cell or plant embryo is a crop, optionally wheat.

In an embodiment, the plant or plant cell expresses a peptide, wherein the peptide:
has at least 50, 60, 70, 80, 90, 95 or 99% sequence identity with GSSHNDLRVRRLT (SEQ ID NO: 12) or RMPQWWQWMWV (SEQ ID NO: 4) or
comprises at least 5, 6, 7 or 8 contiguous amino acids of GSSHNDLRVRRLT (SEQ ID NO: 12) or RMPQWWQWMWV (SEQ ID NO: 4);
optionally wherein the peptide has a maximum length of 30 amino acids.

In an embodiment, the peptide comprises NGSSHNDLRVRRLTLISRLC (SEQ ID NO: 1) or RMPQWWQWMWV (SEQ ID NO: 4), or a conservatively substituted variant thereof.

In an embodiment, the recombinant plant or plant cell has one or more of faster germination rate, increased stress resistance, increased longevity and/or increased hardiness compared to a plant or plant cell not expressing the peptide or compound.

Also provided are various methods including a method of increasing the stress resistance of a mammalian or plant cell or plant, the method comprising:
a. introducing a nucleic acid molecule encoding a peptide described herein, optionally a peptide that has at least 50, 60, 70, 80, 90, 95 or 99% sequence identity with GSSHNDLRVRRLT (SEQ ID NO: 12) or RMPQWWQWMWV (SEQ ID NO: 4) or comprises at least 5, 6, 7 or 8 contiguous amino acids of GSSHNDLRVRRLT (SEQ ID NO: 12) or RMPQWWQWMWV(SEQ ID NO: 4); optionally wherein the peptide has a maximum length of 30 amino acids into a plant or mammal or plant or mammalian cell or plant or mammalian embryo; and
b. growing the plant, mammal, plant or mammalian cell or embryo to obtain a plant, mammal or cell that expresses the peptide.

In an embodiment, the cell, mammal or plant or plant embryo has an increased APC activity optionally measured by a reduction of APC substrate level of at least 10%, at least 20%, at least 30%, at least 40%, at least 50%, at least 60%, at least 70% or at least 80% compared to cell, mammal or plant or plant embryo not expressing the nucleic acid.

In an embodiment, the plant or plant cell or plant embryo has a faster germination rate, increased stress resistance, increased longevity and/or increased hardiness compared to a plant, plant embryo or plant cell not expressing the peptide.

In an embodiment, the cell, embryo or plant has an faster germination rate, increased stress resistance, increased longevity and/or increased hardiness of at least 10%, at least 20%, at least 30%, at least 40%, at least 50%, at least 60%, at least 70% or at least 80% compared to a cell, plant, or embryo, not expressing the nucleic acid.

In an embodiment, the plant is a crop, optionally wheat.

In an embodiment, the vector is suitable for transforming, transducing or infecting plants comprising a nucleic acid molecule encoding a peptide described herein, optionally a peptide that has at least 50, 60, 70, 80, 90, 95 or 99% sequence identity with GSSHNDLRVRRLT (SEQ ID NO: 12) or RMPQWW/VQWMWV (SEQ ID NO: 4) or comprises at least 5, 6, 7 or 8 contiguous amino acids of GSSHNDLRVRRLT (SEQ ID NO: 12) or RMPQW/VQWMWV (SEQ ID NO: 4); optionally wherein the peptide has a maximum length of 30 amino acids.

The present inventor identified and characterized peptides that bind anaphase promoting complex (APC) subunits and/or suppress APC mutant phenotypes, allowing for enhanced stress response and longevity.

The peptides described herein are APC activators. Accordingly, the present disclosure is also directed to use of an APC activator for delaying one or more aging symptoms, increasing lifespan and/or increasing stress resistance.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

DRAWINGS

Embodiments are described below in relation to the drawings in which:

FIG. 1 shows peptides specific for Apc10 suppress APC mutant is growth. A. Y2H cells expressing the APC subunit bait and the galactose inducible Apc10 peptide prey grown on glucose or galactose. Cells co-expressing the Apc5 or Apc10-bait and Apc10 aptamer-prey vectors were spotted onto the appropriate media, in the presence or absence of galactose (the aptamers are Gal inducible), to confirm 2-hybrid interactions. Growth on trp-his-media ensures both plasmids are maintained. A 2-hybrid interaction will drive expression of the ADE2 gene, allowing growth on ade-media. B. Aptamers that bind Apc10 can suppress APC mutant phenotypes. Spot dilutions of apc10Δ cells expressing an empty vector control or the one of 6 Apc10 aptamers tested. Log phase cells were 10-fold serially diluted and spotted onto plates containing either 2% glucose or 2% galactose. The plates were then incubated at 30° C. (permissive temperature) and 34° C. (restrictive stress). C. Peptides identified as binding to the yeast Apc10 APC subunit using the yeast 2-hybrid screen increase growth of cells on stress conditions. A series of APC binding peptides were transformed into wild type yeast cells, spot diluted, and grown at 30° C. on media supplemented with the normal carbon source (2% glucose). Alternatively, cells were grown on media supplemented with 2% galactose to induce a carbon stress. D. Peptides were expressed in $apc5^{ts}$ temperature sensitive cells and grown on glucose or galactose media at 30° C.

FIG. 2 shows Apc10 aptamers increase replicative lifespan and stress resistance. A. $apc5^{CA}$ (temperature sensitive allele) cells were transformed with C43-4, C2-4B or an empty vector. Cells grown overnight in 2% Glu were struck onto 2% Glucose plates and used for the yeast replicative lifespan (RLS) assay. B. Wild type (WT) cells transformed with C43-4, C2-4B or an empty vector were grown to stationary phase in 2% Glu media, then after 2 days spot diluted onto 2% Glu or 2% Gal to induce expression of the aptamers.

Figure 3:
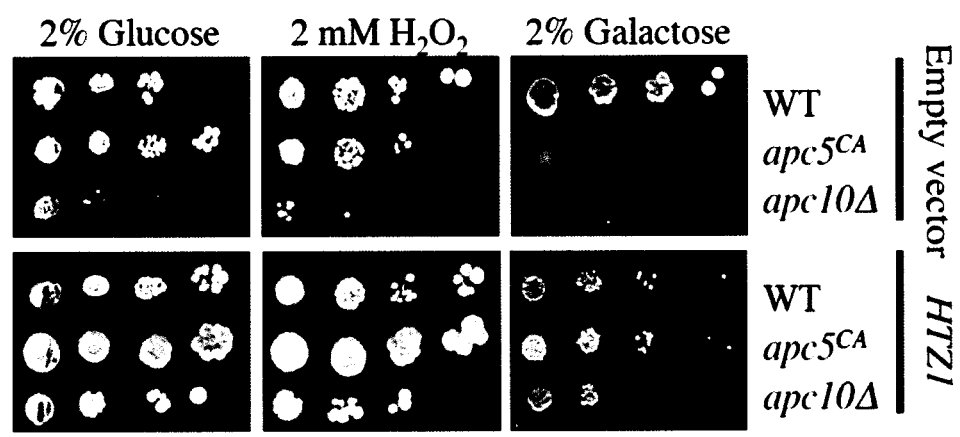

FIG. 3 shows C43-4 and Htz1 extend lifespan and increase stress resistance. A. $apc5^{CA}$ cells expressing small peptides were assayed for replicative life span (RLS). B. Cells expressing HTZ1 were grown under stress conditions. HTZ1 expression, even at low levels, suppresses $apc5^{CA}$ and apc10Δ defects. The cells shown were transformed with either an empty vector or GAL inducible HTZ1. On 2% glucose, the construct is weakly expressed, and this is enough to increase growth of APC mutants at 30° C. HTZ1 at low levels can also suppress oxidative stress defects on $H_2O_2$, and when overexpressed, restore growth on 2% galactose.

FIG. 4 shows Cin5 is unstable and controlled in an opposite manner by the E3's SCF and APC. A. Cin5-TAP is stabilized in SCF and Elc3 E3 mutants. B. Cin5-TAP is further destabilized in cdc20-1 and apc10Δ mutants. CHX stops all protein synthesis. NaCl induces Cin5 protein expression.

Figure 5:
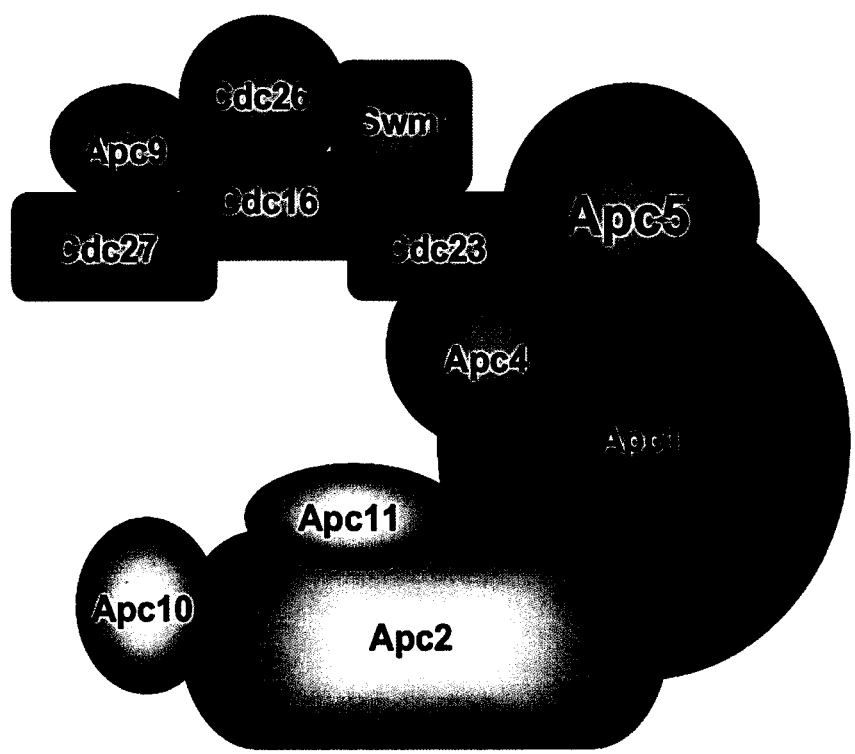

FIG. 5 shows the structure of the yeast Anaphase Promoting Complex (APC). The APC is composed of 2 arms held together by Apc1. The catalytic core of Apc2, Apc10 and Apc11 compose one arm (Thornton et al, 2006).

Figure 6:
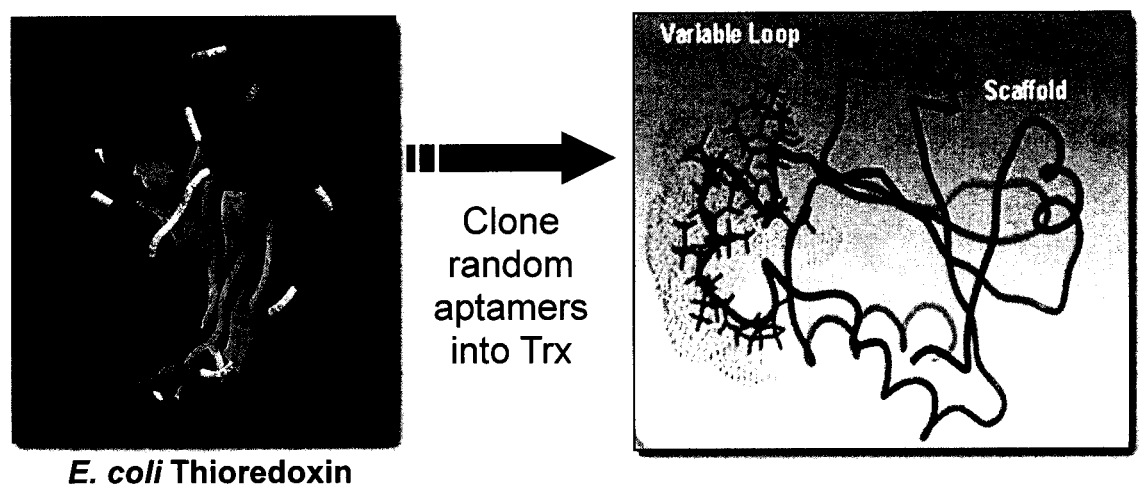

FIG. 6 shows construction of random peptide aptamers for use against yeast proteins. Aptamers are small antibody-like peptide sequences expressed from the Thioredoxin (Trx) scaffold. Random DNA sequences are cloned into Trx to be expressed from the Trx scaffold as the variable loop. This stabilizes the aptamer and presents it to target proteins. Aptamers with specific binding capabilities are selected from large random DNA sequence pools.

FIG. 7 shows a BLAST search for C43-4 homology. The C43-4 aptamer harbors a region homologous to the *Saccharomyces cerevisiae* H2A.Z protein, a histone H2A variant encoded by HTZ1. Incorporation of H2A.Z into nucleosomes prevents spreading of silent chromatin. The homologous region is boxed in gray and is conserved from yeast to humans. Identical residues are bolded. Similar residues are underlined and italicized. Hs—*Homo sapiens*; Mm—*Mus musculus*; Dm—*Drosophila melanogaster*, Sc—*Saccharomyces cerevisiae*.

FIG. 8 shows a BLAST search for C2-4B homology. The C2-4B aptamer shares homology with several *S. cerevisiae* proteins. Ssh3 and Ydl157c are mitochondrial proteins while Pex11 is localized to the peroxisome. Thus, Sum1 is the likely candidate to interact with nuclear APC. Sum1 represses the mitotic expression of meiotic genes and is involved in telomere maintenance and chromatin silencing. The homologous region is boxed in gray. Identical residues are bolded. Similar residues are underlined and italicized. Sc—*Saccharomyces cerevisiae*.

FIG. 9 shows that Htz1 and Sum1 are part of an interaction network. A. STRING network analysis indicates that Htz1 and Sum1 interact within a pathway involving the HDACs Sir2 and Hst1, and the chromatin assembly factors Asf1 and Chz1. B. Htz1 and Sum1 also interact within a network involving Fkh2, a transcription factor that works with the APC to respond to stress and increase lifespan.

Figure 10A:
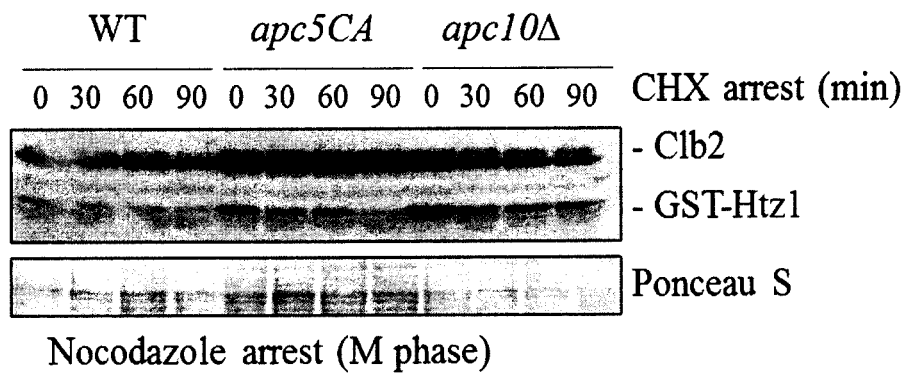
Figure 10B:
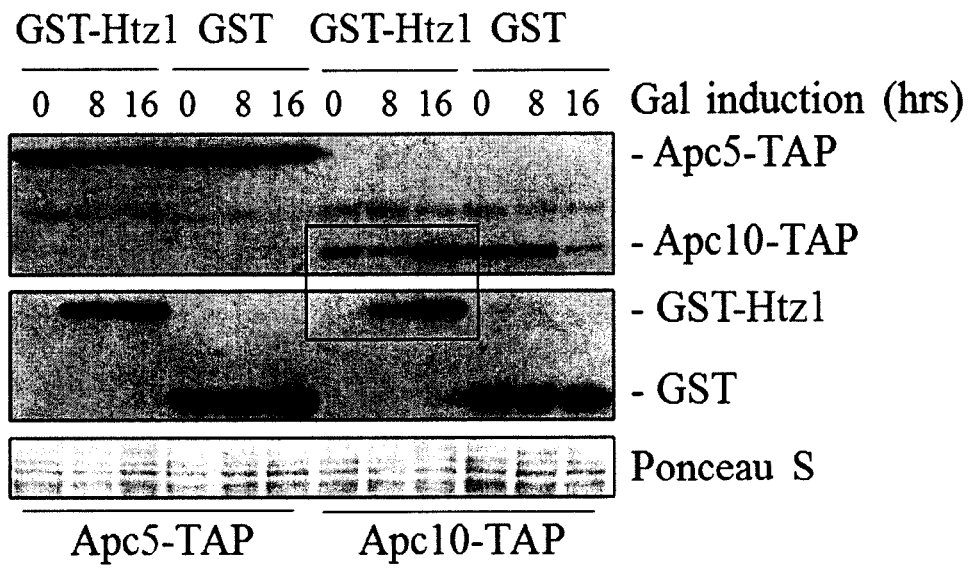

FIG. 10 shows the Apc10-aptamer-like Htz1 is regulated by the APC and drives the expression of Apc10. A. Htz1 accumulates and is unstable in APC mutants during mitosis. The cells shown expressing GST-Htz1 were induced with 0.5% galactose for 16 hours. Nocodazole was added for 3 hours to arrest the cells in mitosis. Cycloheximide (CHX) was then added to inhibit protein synthesis with cells removed at the times shown to assess protein stability. B. Increased expression of Htz1 specifically increases Apc10 protein levels. Apc5-TAP or Apc10-TAP cells expressing Gal inducible GST-Htz1, or the GST empty vector, were grown to mid log phase. 0.5% galactose was added for the time shown followed by GST and TAP westerns. The blue boxed area highlights induction of Apc10-TAP in response to increasing Htz1 levels. Apc5-TAP is unaffected by Htz1 expression.

Figure 11:
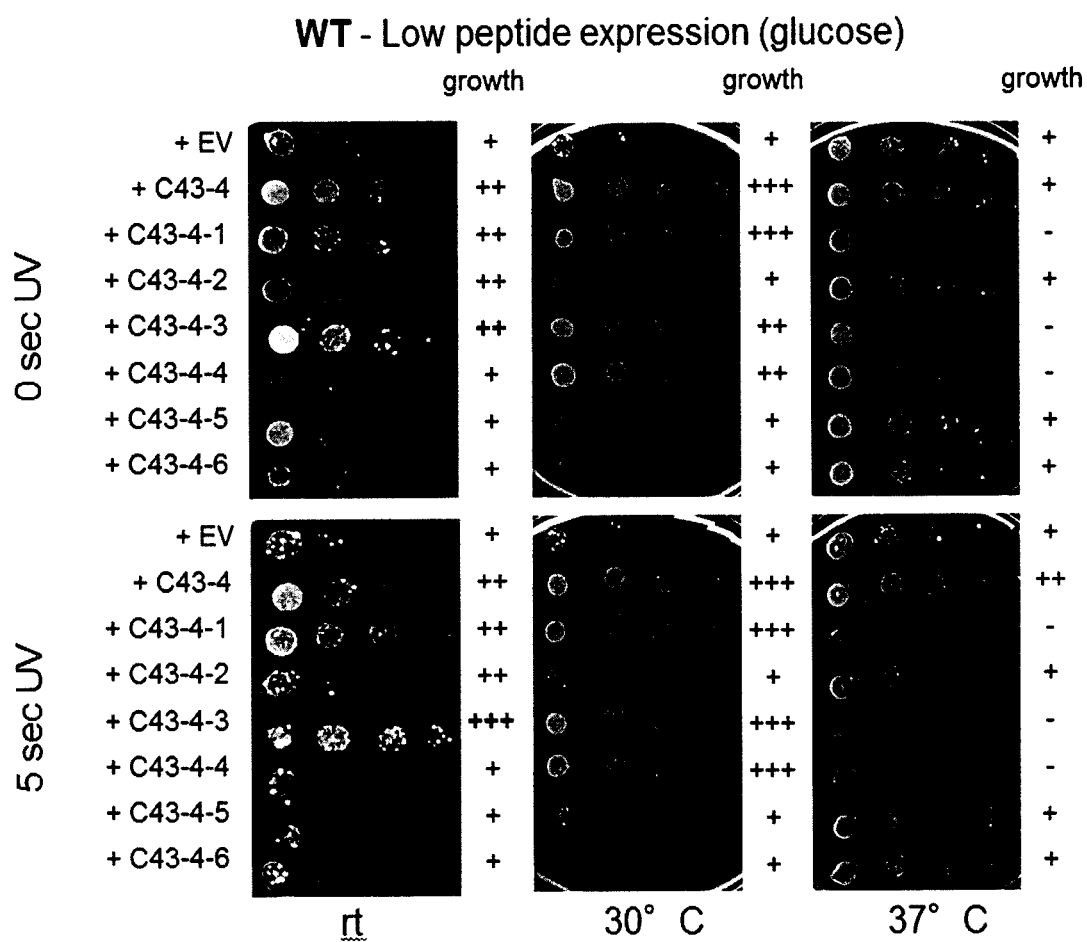

FIG. 11 shows various C43-4 mutant peptides expressed in WT cells and grown on glucose media at the temperatures shown. The cells were exposed to 5 sec of UV from a UV box prior to incubation. The plus signs define growth compared to the empty vector control.

Figure 12:
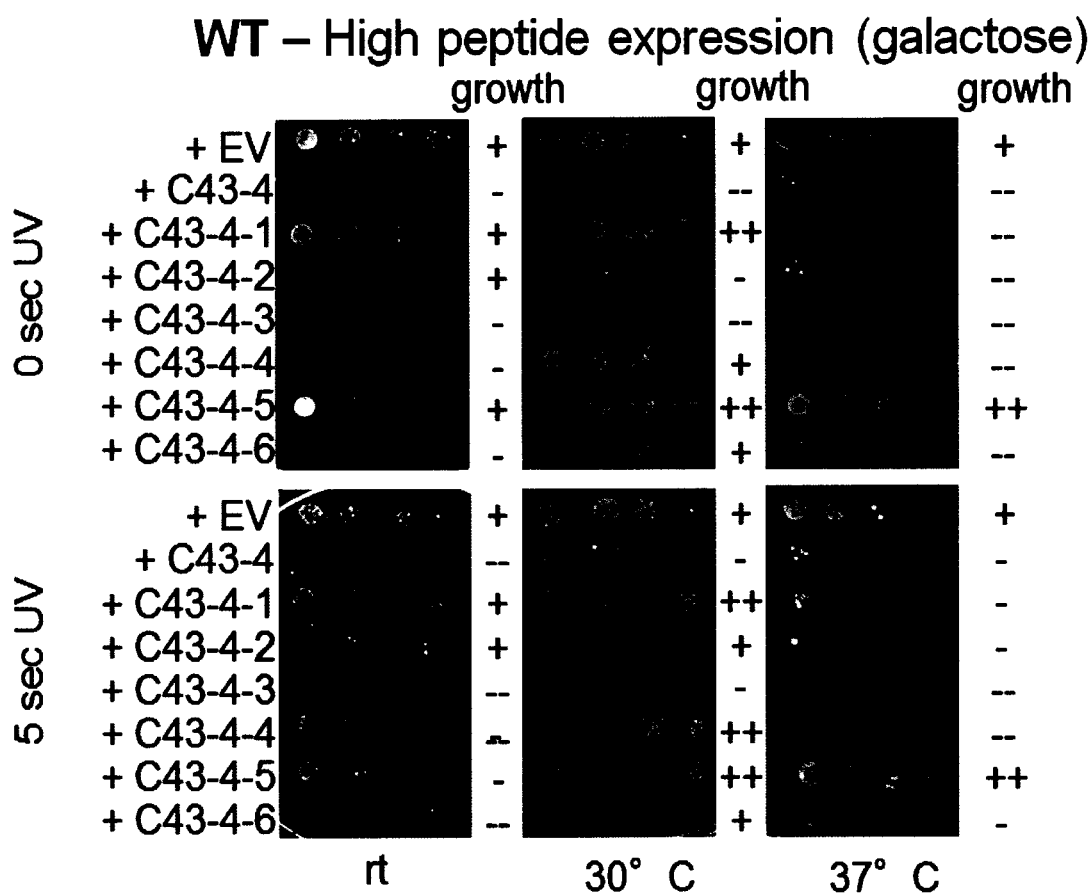

FIG. 12 shows various C43-4 mutant peptides expressed in WT cells and grown on galactose media to induce the peptides at the temperatures shown. The cells were exposed to 5 sec of UV from a UV box prior to incubation. The plus signs define growth compared to the empty vector control.

FIG. 13 shows various C43-4 mutant peptides expressed in apc10Δ cells and grown on glucose or galactose media at the temperatures show. The cells were exposed to 5 sec of UV from a UV box prior to incubation.

FIG. 14 shows C43-4 expressed in wheat embryos localizes to nuclei and reduces the protein levels of an APC substrate. A. Wheat embryos were transformed with an expression vector harboring the C43-4-HA peptide fused to the red fluoresce protein (RFP), or an RFP empty vector, using a ballistic shotgun approach. Embryos were imaged using fluorescence to view RFP. B. Protein lysates were prepared from the transformed embryos and subjected to western analyses using antibodies against the APC substrate Securin. A nonspecific protein band is used to control for protein load.

FIG. 15 shows activation of the APC resensitizes drug resistant cancer cells to chemotherapy. A. M2I-1 exposure (18 hrs) is not toxic, yet combination with Doxorubicin enhances toxicity. A. Parental MCF7 human breast cancer cells, or cells selected for resistance to Tamoxifen, were treated with 1 or 5 µM M2I-1. Tamoxifen resistant cells were also treated with both Doxorubicin and M2I-1. Trypan Blue. (3 rpts). ND, no data. B. Protein lysates were prepared from the cells used in A. The APC target HURP was measured using antibodies against HURP. C. Trypan Blue was used to measure viability of OSW canine lymphoma cells pretreated with 1 µmol M2I-1 (18 hrs), followed by 1 µmol DOX (48 hrs). Parental cells were only treated with monotherapy (3 rpts). ND, no data. D. OSW matched cells treated with the APC activator M2I-1 were prepared for APC substrate westerns E. Quantification of western protein abundance (3 rpts).

Figure 16A:
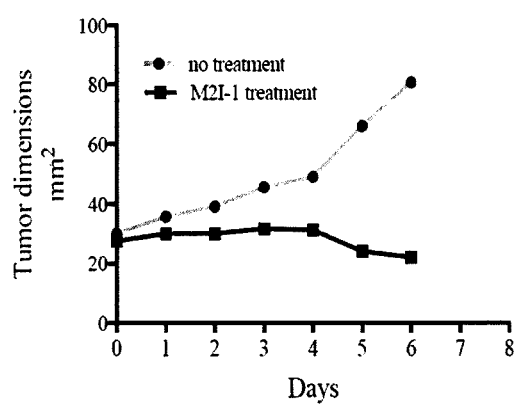
Figure 16B:
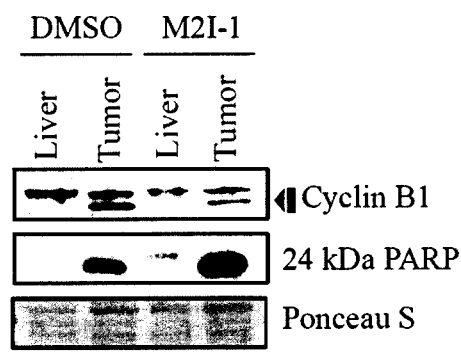

FIG. 16 shows M2I-1 stalls the growth of tumor cells in a mouse model of TNBC. A. In vivo study of M2I-1 impact on human breast tumor (4-28 PDX). Single 25 mg/kg i.p. injection (treatment) versus mock (DMSO) day 1, tumor size measured daily. B. Western analysis of apoptosis (PARP cleavage—24 kDa band) and APC substrate abundance (Cyclin B) in liver and tumor of treated and control after sacrifice on Day 6.

DESCRIPTION OF VARIOUS EMBODIMENTS

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used herein, the terms "subject" and "animal" include all members of the animal kingdom that comprise an anaphase promoting complex, including yeast and other eukaryotes. In one embodiment, the subject is a mammal. In another embodiment, the subject is a fish or a bird. In a further embodiment, the subject is a human being.

The term "a cell" includes a single cell as well as a plurality or population of cells. Cells contemplated with the present disclosure include microbial cells such as bacterial or yeast cells, plant cells and mammalian cells.

The term "embryo" includes a seed.

Compositions of Matter:

Peptides, Nucleic acids, Vectors and Recombinant Cells

The present inventor has identified several novel non-naturally occurring peptides also referred to as aptamers herein that can bind a subunit of defective anaphase promoting complex (APC) and/or activate APC.

Accordingly, in one aspect, the disclosure provides a peptide. As shown herein, the peptides described can increase the viability of cells with defective anaphase promoting complex (APC) function and/or specifically bind the APC. As used herein, the term "anaphase promoting complex (APC)" refers to the large evolutionarily conserved complex found in yeast and human that is required for stress resistance an extended lifespan by targeting proteins that promote aging for degradation. The APC is a ubiquitin protein ligase required for mitotic progression and G1 maintenance. The APC is also necessary for stress response, chromatin assembly, histone biogenesis and longevity in yeast (Harkness et al, 2004; Postnikoff et al, 2012; Harkness et al, 2002; Turner et al, 2010).

Peptides identified by the present inventor are set out in Tables 1 and 2 (SEQ ID NOs: 1-17).

As used herein, the term "peptide" refers to two or more amino acids linked by a peptide bond, and includes synthetic and natural peptides as well as peptides that are modified. Various lengths of peptides are contemplated herein.

The peptide can for example be 5-50 amino acids in length, optionally 7-30 amino acids in length or at least 25 or 30 amino acids in length. The peptide can for example be any number of amino acids between 5 and 30.

Accordingly, in one embodiment, the peptide comprises an amino acid sequence as shown in any one of SEQ ID NOs: 1-17, or a conservatively substituted variant thereof.

Also provided is a peptide that is a part of a sequence described herein, optionally a part of any one of SEQ ID NO: 1 to 17.

The term "part" with reference to amino acids means at least 5 contiguous amino acids of the reference sequence. The reference sequence can for example by any one of SEQ ID NO: 1-17, or a conservatively substituted variant thereof.

In another embodiment, the peptide consists essentially of, or consists of an amino acid sequence as shown in any one of SEQ ID NOs: 1-17, or a conservatively substituted variant thereof.

In another embodiment, the peptide comprises at least 30, 40, 50, 60, 70, 80, 90, 95 or 99% sequence identity with the amino acid sequence as shown in any one of SEQ ID NOs: 1-17 or a part thereof. In another embodiment, the peptide comprises or consists of an amino acid sequence comprising at least 5, 6, 7 or 8 contiguous amino acids of SEQ ID NOs: 1-17.

In particular, the inventor identified peptide "C43-4" having the amino acid sequence set out in SEQ ID NO: 1. Peptide "C43-4" binds Apc10 in a yeast 2 hybrid assay and increases the viability of an APC mutant. Residues 2-14 of SEQ ID NO: 1 (SEQ ID NO: 12) have homology with histone variant Htz1 in yeast (human H2AZ).

Accordingly, the disclosure provides a peptide that has at least 50, 60, 70, 80, 90, 95 or 99% sequence identity with GSSHNDLRVRRLT (SEQ ID NO: 12) or NGSSHNDLRVRRLTLISRLC (SEQ ID NO: 22). In another embodiment, the peptide comprises at least 5, 6, 7 or 8 contiguous amino acids of GSSHNDLRVRRLT (SEQ ID NO: 12) or NGSSHNDLRVRRLTLISRLC (SEQ ID NO: 22). In another embodiment, the peptide comprises or GSSHNDLRVRRLT (SEQ ID NO: 12) or NGSSHNDLRVRRLTLISRLC (SEQ ID NO: 22). In a further embodiment, the peptide comprises an amino acid sequence that has at least 30, 40, 50, 60, 70, 80, 90, 95 or 99% sequence identity with a corresponding Htz1 fragment.

A variant of peptide "C43-4" is also provided, wherein the leucine residue at position 8 is replaced with alanine (SEQ ID NO: 2) (peptide "C43-4-3"). Peptide "C43-4-3" binds Apc10 in a yeast 2 hybrid assay. In one embodiment, the peptide increases cell viability for example as measured in an APC mutant assay by at least 5%, 10%, 20%, 30%, 40%, 50%, 60%, 70%, 80%, 90% or 100% compared to "C43-4". As shown in the Figures such as FIG. 11, C43-4-3 expressing cells show increased growth and increased resistance to UV stress compared to C43-4 cells for example at room temperature. Each spot from left to right contains 10 fold less cells. Growth of an increased number of colonies in UV treated C43-4-3 expressing cells compared to C43-4 expressing cells is shown. The inventor has also shown that residues 7, 12 and 14 of SEQ ID NO: 1 are important for peptide function. Other variants of C43-4 are also provided.

Thus, in one embodiment, the disclosure provides a peptide, wherein the peptide comprises amino acid sequence XSSHXDAXXXRXT (SEQ ID NO: 24), wherein X is any amino acid and the peptide has a maximum length of 30 amino acids, or a conservatively substituted variant thereof. In another embodiment, the peptide comprises or consists of GSSHNDARVRRLT (SEQ ID NO: 34), or a conservatively substituted variant thereof. In another embodiment, the peptide comprises or consists of NGSSHNDARVRRLTLISRLC (SEQ ID NO: 20), or a conservatively substituted variant thereof. In one embodiment, the peptide has an alanine residue at the amino acid corresponding to position 8 of SEQ ID NO: 2. In another embodiment, the peptide does not have an leucine residue at the amino acid corresponding to position 8 of SEQ ID NO: 2.

As used herein, the term "conservatively substituted variant" refers to a variant with at least one conservative amino acid substitution. A "conservative amino acid substitution" as used herein, refers to the substitution of an amino acid with similar hydrophobicity, polarity, and R-chain length for one another. In a conservative amino acid substitution, one amino acid residue is replaced with another amino acid residue without abolishing the protein's desired properties. Without the intention of being limited thereby, in one embodiment, the substitutions of amino acids are made that preserve the structure responsible for the ability to increase the viability of a cell with defective anaphase promoting complex (APC) function and/or bind to the APC as disclosed herein. Examples of conservative amino acid substitutions include:

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The inventor further identified peptide "02-4B" having the amino acid sequence set out in SEQ ID NO. 4. Peptide "02-4B" binds Apc5 in a yeast 2 hybrid assay and increases the viability of an APC mutant. In one embodiment, the peptide increases cell viability for example as measured in an APC mutant assay by at least 5%, 10%, 20%, 30%, 40%, 50%, 60%, 70%, 80%, 90% or 100% compared to "C43-4". C2-4B has homology with Sum1 in yeast. Thus, in another embodiment, the peptide comprises an amino acid sequence that has at least 30, 40, 50, 60, 70, 80, 90, 95 or 99% sequence identity with a corresponding fragment of Sum1. In addition, residues 1-9 of C2-4B (SEQ ID NO: 14) have homology with Naf1 in yeast (human NAF1). Thus, in another embodiment, the peptide comprises an amino acid sequence that has at least 30, 40, 50, 60, 70, 80, 90, 95 or 99% sequence identity with a corresponding fragment of Naf1.

Thus, in another embodiment, the disclosure provides a peptide that has at least 50, 60, 70, 80, 90, 95 or 99% sequence identity with RMPQWWQWM (SEQ ID NO: 14) or RMPQWWQWMWV (SEQ ID NO: 4). In another embodiment, the peptide comprises at least 5, 6, 7 or 8 contiguous amino acids of RMPQWWQWM (SEQ ID NO: 14) or RMPQWWQWMWV (SEQ ID NO: 4). In another embodiment, the peptide comprises or consists of RMPQWWQWM (SEQ ID NO: 14) or RMPQWWQWMWV (SEQ ID NO: 16).

The inventor also identified a peptide having the amino acid set out in SEQ ID NO. 3. This peptide binds Apc5 in a yeast 2 hybrid assay and increases the viability of an APC mutant. In one embodiment, the peptide increases cell viability for example as measured in an APC mutant assay by at least 5%, 10%, 20%, 30%, 40%, 50%, 60%, 70%, 80%, 90% or 100% compared to "C43-4". Residues 5-19 of SEQ ID NO: 3 (SEQ ID NO: 13) have homology with Swe1 in yeast (human Wee1).

Thus, in another embodiment, the disclosure provides a peptide, wherein the peptide comprises amino acid sequence ETETFHPITRHLIVP (SEQ ID NO: 13) and the peptide has a maximum length of 30 amino acids, or a conservatively substituted variant thereof. In another embodiment, the peptide comprises or consists of CECLETETFHPITRHLIVPV (SEQ ID NO: 3), or a conservatively substituted variant thereof. In another embodiment, the peptide has at least 50, 60, 70, 80, 90, 95 or 99% sequence identity with ETETFHPITRHLIVP (SEQ ID NO: 13) or CECLETETFHPITRHLIVPV (SEQ ID NO: 3). In yet another embodiment, the peptide comprises at least 5, 6, 7, or 8 contiguous amino acids of ETETFHPITRHLIVP (SEQ ID NO: 13) or CECLETETFHPITRHLIVPV (SEQ ID NO: 3). In another embodiment, the peptide comprises an amino acid sequence that has at least 30, 40, 50, 60, 70, 80, 90, 95 or 99% sequence identity with a corresponding fragment of Swe1.

The inventor further identified a peptide having the amino acid set out in SEQ ID NO. 5. This peptide binds Apc10 in a yeast 2 hybrid assay and increases the viability of an APC mutant. In one embodiment, the peptide increases cell viability for example as measured in an APC mutant assay by at least 5%, 10%, 20%, 30%, 40%, 50%, 60%, 70%, 80%, 90% or 100% compared to "C43-4". Residues 16-25 of SEQ ID NO: 5 (SEQ ID NO: 15) have homology with Rrp9 in yeast (human RRP9). In addition, residues 15-21 of SEQ ID NO: 5 (SEQ ID NO: 16) have homology with Hos2 in yeast (human HOS2). In addition, residues 2-21 of SEQ ID NO: 5 (SEQ ID NO: 17) have homology with Hap1 in yeast.

Accordingly, the disclosure provides a peptide comprising amino acid sequence HPRRQPKRPI (SEQ ID NO: 15), amino acid sequence THGGRHP (SEQ ID NO: 16) or amino acid sequence SYNTIKYHETHGGRHPRRQP (SEQ ID NO: 17) and wherein the peptide has a maximum length of 30 amino acids. In another embodiment, the peptide comprises or consists of PSYNTIKYHETHGGRHPRRQPKRPI (SEQ ID NO: 5), or a conservatively substituted variant thereof. In another embodiment, the peptide has at least 50, 60, 70, 80, 90, 95 or 99% sequence identity with PSYNTIKYHETHGGRHPRRQPKRPI (SEQ ID NO: 5). In yet another embodiment, the peptide comprises at least 5, 6, 7, or 8 contiguous amino acids of PSYNTIKYHETHGGRHPRRQPKRPI (SEQ ID NO: 5). In another embodiment, the peptide comprises an amino acid sequence that has at least 30, 40, 50, 60, 70, 80, 90, 95 or 99% sequence identity with a corresponding fragment of Rrp9. Thus, in another embodiment, the peptide comprises an amino acid sequence that has at least 30, 40, 50, 60, 70, 80, 90, 95 or 99% sequence similarity with a corresponding fragment of Hos2. Thus, in another embodiment, the peptide comprises an amino acid sequence that has at least 30, 40, 50, 60, 70, 80, 90, 95 or 99% sequence identity with a corresponding fragment of Hap1

The inventor also identified a peptide having the amino acid set out in SEQ ID NO. 6. This peptide binds Apc5 in a yeast 2 hybrid assay and increases the viability of an APC mutant. In one embodiment, the peptide increases cell viability for example as measured in an APC mutant assay by at least 5%, 10%, 20%, 30%, 40%, 50%, 60%, 70%, 80%, 90% or 100% compared to "C43-4". This peptide has homology with yeast proteins Mad2, Hxt2 and/or Ubc7.

Accordingly, the disclosure provides a peptide comprising or consisting of GALKEVCICIVESVGGEVFSGP (SEQ ID NO: 6), or a conservatively substituted variant thereof. In another embodiment, the peptide has at least 50, 60, 70, 80, 90, 95 or 99% sequence identity with GALKEVCICIVESVGGEVFSGP (SEQ ID NO: 6). In yet another embodiment, the peptide comprises at least 5, 6, 7, or 8 contiguous amino acids of GALKEVCICIVESVGGEVFSGP (SEQ ID NO: 6). In another embodiment, the peptide comprises an amino acid sequence that has at least 30, 40, 50, 60, 70, 80, 90, 95 or 99% sequence identity with a corresponding fragment of Mad2, Hxt2 and/or Ubc7.

The inventor also identified a peptide having the amino acid sequence set out in SEQ ID NO: 7. This peptide binds Apc5 in a yeast 2 hybrid assay and increases the viability of an APC mutant. The following motifs of interest this were also identified: SKWT and MOMS.

Thus, in one embodiment, a peptide comprising the amino acid motifs SKWT and MOMS is provided. In another embodiment, the peptide comprises or consists of SKWTWRMCMSWTVDRFAPVPWP (SEQ ID NO: 7), or a conservatively substituted variant thereof. In another embodiment, the peptide has at least 50, 60, 70, 80, 90, 95 or 99% sequence identity with SKWTWRMCMSWTVDR-FAPVPWP (SEQ ID NO: 7). In yet another embodiment, the peptide comprises at least 5, 6, 7, or 8 contiguous amino acids of SKWTWRMCMSWTVDRFAPVPWP (SEQ ID NO: 7).

The inventor further identified a peptide having the amino acid sequence set out in SEQ ID NO: 8. This peptide binds Apc10 in a yeast 2 hybrid assay and increases the viability of an APC mutant. In one embodiment, the peptide increases cell viability for example as measured in an APC mutant assay by at least 5%, 10%, 20%, 30%, 40%, 50%, 60%, 70%, 80%, 90% or 100% compared to "C43-4". The following motifs of interest in this peptide were also identified: PRP (SEQ ID NO: 38) and PPL (SEQ ID NO: 39).

Thus, in one embodiment, a peptide comprising the amino acid motifs PRP and PPL is provided. In another embodiment, the peptide comprises or consists of GRMLMTYLMYFMVLWVPRPWGPPL (SEQ ID NO: 8), or a conservatively substituted variant thereof. In another embodiment, the peptide has at least 50, 60, 70, 80, 90, 95 or 99% sequence identity with GRMLMTYLMYFMVLWVPRPWGPPL (SEQ ID NO: 8). In yet another embodiment, the peptide comprises at least 5, 6, 7, or 8 contiguous amino acids of GRMLMTYLMYFMVLWVPRPWGPPL (SEQ ID NO: 8).

The inventor also identified a peptide having the amino acid sequence set out in SEQ ID NO: 9. This peptide binds Apc10 in a yeast 2 hybrid assay and increases the viability of an APC mutant. In one embodiment, the peptide increases cell viability for example as measured in an APC mutant assay by at least 5%, 10%, 20%, 30%, 40%, 50%, 60%, 70%, 80%, 90% or 100% compared to "C43-4".

Thus, in one embodiment, a peptide comprising or consisting of RRCLSIRTENLAWEGKFLRV (SEQ ID NO: 9), or a conservatively substituted variant thereof is provided. In another embodiment, the peptide has at least 50, 60, 70, 80, 90, 95 or 99% sequence identity with RRCLSIRTEN-LAWEGKFLRV (SEQ ID NO: 9). In yet another embodiment, the peptide comprises at least 5, 6, 7, or 8 contiguous amino acids of RRCLSIRTENLAWEGKFLRV (SEQ ID NO: 9).

Using a reverse genetic screen, the inventor also identified a group of peptides that rescue apc5 temperature sensitive (ts) growth but do not bind the APC. Two of these peptides are identified as "Y65" and "Y36" in the present disclosure.

In particular, peptide "Y65" having the amino acid set out in SEQ ID NO: 10 is provided. This peptide increases the viability of an apc5 temperature sensitive (ts) growth mutant. In one embodiment, the peptide increases cell viability for example as measured in an APC mutant assay by at least 5%, 10%, 20%, 30%, 40%, 50%, 60%, 70%, 80%, 90% or 100% compared to "C43-4". This peptide has homology with yeast protein Elc1.

Thus, in one embodiment, a peptide having at least 50, 60, 70, 80, 90, 95 or 99% sequence identity with VRQKSD-KEYERVLGLGLRR (SEQ ID NO: 41) is provided. In one embodiment, the peptide increases the viability of an apc5 temperature sensitive (ts) growth mutant, and has a maximum length of 30 amino acids. In another embodiment, the peptide comprises or consists of VRQKSDKEY-ERVLGLGLRR (SEQ ID NO: 41), or a conservatively substituted variant thereof. In another embodiment, the peptide has at least 50, 60, 70, 80, 90, 95 or 99% sequence identity with VRQKSDKEYERVLGLGLRR (SEQ ID NO: 41). In yet another embodiment, the peptide comprises at least 5, 6, 7, or 8 contiguous amino acids of VRQKSDKEY-ERVLGLGLRR (SEQ ID NO: 41). In a further embodiment, the peptide comprises an amino acid sequence that has at least 30, 40, 50, 60, 70, 80, 90, 95 or 99% sequence or identity with Elc1 or a fragment thereof.

The "Y36" having the amino acid sequence set out in SEQ ID NO: 11 is also provided. This peptide increases the viability of an apc5 temperature sensitive (ts) growth mutant. In one embodiment, the peptide increases cell viability for example as measured in an APC mutant assay by at least 5%, 10%, 20%, 30%, 40%, 50%, 60%, 70%, 80%, 90% or 100% compared to "C43-4". This peptide has homology with yeast proteins Tim17, Sit4, Iml3, Scc4 (cohesin complex) and Ngs1.

Thus, in one embodiment, a peptide having at least 50, 60, 70, 80, 90, 95 or 99% sequence identity with SWLNGSGGVVLWLFSNFCCG (SEQ ID NO: 11) is provided. In one embodiment, the peptide increases the viability of an apc5 temperature sensitive (ts) growth mutant, and has a maximum length of 30 amino acids. In another embodiment, the peptide comprises or consists of SWLNGSGGVVLWLFSNFCCG (SEQ ID NO: 11), or a conservatively substituted variant thereof. In another embodiment, the peptide has at least 50, 60, 70, 80, 90, 95 or 99% sequence identity with SWLNGSGGVVLWLF-SNFCCG (SEQ ID NO: 11). In yet another embodiment, the peptide comprises at least 5, 6, 7, or 8 contiguous amino acids of SWLNGSGGVVLWLFSNFCCG (SEQ ID NO: 11). In a further embodiment, the peptide comprises an amino acid sequence that has at least 30, 40, 50, 60, 70, 80, 90, 95 or 99% sequence identity with Tim17, Sit4, Iml3, Scc4 and/or Ngs1 or a fragment thereof.

In one embodiment, peptides having at least 30, 40, 50, 60, 70, 80, 90, 95 or 99% sequence identity with SEQ ID NOs: 1-17 have the same function and/or activity as peptides consisting of SEQ ID NOs: 1-17. In one embodiment, a peptide having at least 30, 40, 50, 60, 70, 80, 90, 95 or 99% sequence identity with SEQ ID NOs: 1-17 increases the viability of an apc5 temperature sensitive (ts) growth mutant and/or binds to the APC.

As used herein, the expression "increases the viability of an APC mutant" refers to increasing the cell viability of a cell with defective anaphase promoting complex (APC) function. Examples of yeast cells with defective anaphase promoting complex (APC) function include apc5 and apc10 mutants. An example of an apc5 mutant is the apc5 temperature sensitive mutant described herein. An example of an apc10 mutant is the apc10 deletion mutant described herein. Viability is optionally increased by at least 5%, 10%, 20%, 30%, 40%, 50%, 60%, 70%, 80%, 90% or 100% compared to a cell with wild-type APC function.

As used herein, the expression "binds to the APC" refers to a peptide that binds to at least one subunit of the APC, for example Apc5 or Apc10. Binding can be measured for example, by any method known in the art, including, but not limited to a yeast 2-hybrid assay.

Sequence identity can be calculated according to methods known in the art. Sequence identity is most preferably assessed by the algorithm of BLAST version 2.1 advanced search. BLAST is a series of programs that are available, for example, online from the National Institutes of Health. The advanced blast search is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J.

Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schiffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656. In addition, percent identity or homology between two sequences may be determined by comparing a position in the first sequence with a corresponding position in the second sequence. When the compared positions are occupied by the same nucleotide or amino acid, as the case may be, the two sequences are conserved at that position. The degree of conservation between two sequences is often expressed, as it is here, as a percentage representing the ratio of the number of matching positions in the two sequences to the total number of positions compared.

One or more amino acid insertions may be introduced into the amino acid sequences shown in SEQ ID NOs: 1-17. Amino acid insertions may consist of single amino acid residues or sequential amino acids ranging from 2 to 15 amino acids in length.

Deletions may consist of the removal of one or more amino acids, or discrete portions from the amino acid sequence shown in SEQ ID NOs: 1-17. The deleted amino acids may or may not be contiguous. The lower limit length of the resulting analog with a deletion mutation is at least 6, 7 or 8 amino acids.

Exemplary methods of making the alterations set forth above are disclosed by Sambrook et al (Molecular Cloning: A Laboratory Manual, 2nd Ed., Cold Spring Harbor Laboratory Press, 1989).

In another embodiment, the peptides described herein are modified for cell permeability, improved stability, and better bioavailability. These modifications include, without limitation, peptide conjugation, peptide cyclization, peptide end modification (e.g. N-acetylation or C-amidation, side chain modifications including the incorporation of non-coded amino acids or non-natural amino acids, N-amide nitrogen alkylation, chirality changes (incorporation of or replacement of L-amino acids with D-amino acids), generation of pseudopeptides (e.g. amide bond surrogates), or peptoids, or azapeptides or azatides). In one embodiment, the peptides described herein are modified by the addition of a lipophilic moiety.

The peptides described above may be prepared using recombinant DNA methods. These peptides may be purified and/or isolated to various degrees using techniques known in the art. Accordingly, nucleic acid molecules having a sequence which encodes a peptide of the disclosure may be incorporated according to procedures known in the art into an appropriate expression vector which ensures good expression of the protein. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule encoding a peptide of the disclosure and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

Alternatively, the peptides can be prepared by chemical synthesis using techniques well known in the chemistry of proteins such as solid phase synthesis [Merrifield 1964] or synthesis in homogeneous solution [Houbenwycl, 1987].

The peptides maybe modified with a detectable label.

The term "detectable label" as used herein refers to moieties such as peptide sequences (such a myc tag, HA-tag, V5-tag or NE-tag), fluorescent proteins that can be appended or introduced into a peptide or compound described herein and which is capable of producing, either directly or indirectly, a detectable signal. For example, the label may be radio-opaque, or a radioisotope, such as $^3H$, $^{13}N$, $^{14}C$, $^{18}F$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The peptides may also be modified with an enhancer moiety. Accordingly, another aspect provides a compound comprising a peptide described herein and an enhancer moiety. In one embodiment, the peptide is conjugated directly or indirectly to the enhancer moiety. As used herein, an enhancer moiety can increase or enhance the activity of the engineered peptide. For example, the enhancer may be a permeability enhancer, a stability enhancer or a bioavailability enhancer. The enhancer moiety is optionally selected from a protein carrier, or a polymer carrier. In one embodiment, the enhancer moiety is a carrier protein, thereby forming a fusion protein. In another embodiment, the enhancer moiety is a PEG moiety.

The peptides described herein can also be conjugated to a carrier protein, thereby forming a fusion protein.

The disclosure also includes nucleic acids that encode the peptides described herein. As used herein, the term "nucleic acids" includes isolated nucleic acids.

In one embodiment, the disclosure provides nucleic acids that encode a peptide comprising or consisting of any one of SEQ ID NOs: 1-17 or any peptide described herein.

In another embodiment the disclosure provides a nucleic acid having at least 30, 40, 50, 60, 70, 80, 90, 95 or 99% sequence identity with a nucleic acid that encodes a peptide comprising or consisting of any one of SEQ ID NOs: 1-17, a nucleic acid that hybridizes to a nucleic acid that encodes a peptide comprising or consisting of any one of SEQ ID NOs: 1-17 or any peptide described herein under at least moderately stringent hybridization or stringent hybridization conditions, wherein the. peptide increases the viability of a cell with defective anaphase promoting complex (APC) function.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature ($Tm=81.5°$ C.$-16.6$ (Log 10 [Na+])$+0.41$(% (G+C)$-600/l$), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a>95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5×sodium chloride/sodium citrate (SSC)/5×Denhardt's solution/1.0% SDS at Tm (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Ausubel, 1989 and in: Sambrook et al., 1989.

The disclosure further contemplates a vector comprising a nucleic acid described herein, optionally a recombinant expression vector containing a nucleic acid molecule that encodes a peptide of the disclosure and the necessary regulatory sequences for the transcription and translation of the inserted protein-sequence.

The recombinant expression vectors of the disclosure may also contain a selectable marker gene that facilitates the selection of host cells transformed or transfected with a recombinant molecule of the disclosure. Examples of selectable marker genes are genes encoding a protein which confers resistance to certain drugs, such as G418 and hygromycin.

In one embodiment, the vector is a plant vector. As used herein, the term "plant vector" means a nucleic acid molecule, such as a plasmid, comprising regulatory elements and a site for introducing transgenic DNA, which is used to introduce said transgenic DNA into a plant. The plant vector may be for example a T-DNA plasmid of *A. tumefaciens*, pBIN19, pPZP100 or a vector of the pCAMBIA series. Additional plant vectors are described in the literature.

The plant vectors may also contain other elements suitable for the proper expression of the protein in the plant or plant cell. In particular, each vector may also contain a promoter that promotes transcription in plants or plant cells. Suitable promoters include, but are not limited to, cauliflower mosaic virus promoters (such as CaMV35S and 19S), nopaline synthase promoters, alfalfa mosaic virus promoter, and other plant virus promoters. Constitutive promoters, such as plant actin gene promoters, and histone gene promoters can also be used.

The plant vectors may also contain suitable terminators useful for terminating transcription in the plant or plant cell. Examples of terminators include the nopaline synthase poly A addition sequence (nos poly A), cauliflower mosaic virus 19S terminator, actin gene terminator, alcohol dehydrogenase gene terminator, or any other terminator from the GenBank database.

In another embodiment, the vector is a viral vector such as a retroviral, lentiviral, adenoviral or adeno-associated viral vector.

Recombinant expression vectors can be introduced into host cells to produce a transformed host cell. The term "transformed host cell" is intended to include prokaryotic and eukaryotic cells which have been transformed or transfected with a recombinant expression vector of the disclosure. The terms "transformed with", "transfected with", "transformation" and "transfection" are intended to encompass introduction of nucleic acid (e.g. a vector) into a cell by one of many possible techniques known in the art.

Recombinant cells can also be prepared expressing the peptides described herein

The recombinant cell can be for preparing recombinant peptide. Suitable host cells include a wide variety of prokaryotic and eukaryotic host cells. For example, the proteins of the disclosure may be expressed in bacterial cells such as *E. coli*, insect cells (using baculovirus), yeast cells or mammalian cells, COS1 cells. Other suitable host cells can be found in Goeddel, Gene Expression Technology: Methods in Enzymology 185, Academic Press, San Diego, Calif. (1991).

Also provided in another aspect is a recombinant cell expressing a peptide, nucleic acid, vector or compound described herein. In an embodiment, the cell is a yeast cell, a mammalian cell, a plant cell.

In an embodiment, the plant cell is selected from a wheat, rapeseed, alfalfa, barley, canola, flax, rye, oat, vegetable plant cells, fruit plant cell or a tobacco plant cell. In another embodiment, the cell is an *Arapidopsis* plant cell.

A further aspect is a recombinant embryo, optionally a seed. Methods for preparing recombinant mammalian embryos can include transgene introduction of a vector, For example, the method can include transforming embryonic stem cells (ES cells) growing in tissue culture with the desired DNA; or injecting the desired gene into the pronucleus of a fertilized non-human egg, optionally a mouse or other rodent.

A further aspect of the invention is a recombinant plant, yeast or mammal expressing a peptide, nucleic acid vector or compound disclosed herein. These can be prepared for example from recombinant cells and/or embryos described herein or prepared using plants and mammals, for example using topical formulations of nucleic acids and vectors described herein.

In one embodiment, the recombinant yeast cell has decreased levels of Cin5 gene or protein expression compared to a non-recombinant yeast cell. Optionally, the recombinant yeast cell has at least 5, 10, 15, 20, 25, 50, 75, 90, 95 or 100% less Cin5 protein compared to a non-recombinant yeast cell. Levels of Cin5 gene or protein expression may be determined by any method known in the art.

Recombinant plants and seeds can be prepared using known methods in the art, including for example cell-culture-based systems that are equivalent to mammalian, microbial and insect cell systems; transient expression of foreign genes in plant tissues that are transformed by either agroinjection or by viral infection and development of transgenic plants carrying stably integrated transgenes.

Compositions

The disclosure also provides a composition, optionally a pharmaceutical composition, comprising the peptides, nucleic acids and recombinant cells described herein.

In an embodiment, the composition comprises a carrier or diluent.

The carrier can optionally be a pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin and bovine serum albumin (BSA).

A pharmaceutical composition is formulated to be compatible with its intended route of administration. Examples of routes of administration include parenteral, e.g. intravenous, intradermal, subcutaneous, oral (e.g. inhalation), transdermal (i.e., topical), transmucosal, and rectal administration.

In one embodiment, the active ingredient is prepared with a carrier that will protect it against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In one embodiment, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms are dictated by and directly dependent on the unique characteristics of the active ingredient and the particular therapeutic effect to be achieved, and the limitations inherent in the art of preparing such an active ingredient for the treatment of individuals.

The formulation can also contain more than one active ingredient as necessary for the particular indication being treated, optionally those with complementary activities that do not adversely affect each other. Alternatively, or in addition, the pharmaceutical composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

Methods and Uses

The disclosure also provides uses and methods relating to APC activators.

As used herein, the term activator of the Anaphase Promoting Complex (APC) or "APC activator" refers to substance that increases the activity of the Anaphase Promoting Complex, measurable for example by a decrease in an APC substrate, preferably multiple APC substrates.

In one embodiment, the APC activator decreases the level of at least one of APC substrate by at least 10%, at least 20%, at least 30%, at least 40%, at least 50%, at least 60%, at least 70% or at least 80% compared to a cell, plant, embryo, or cell of a subject not contacted, introduced or administered the activator.

As used herein, the term "APC substrate" refers to a protein that the APC targets for degradation. Examples of APC substrates include, but are not limited to, securin, cyclin B1, HURP and CDC20.

In another embodiment, the APC activator increases the cell viability of an APC mutant cell, plant, embryo, or cell of a subject by at least 10%, at least 20%, at least 30%, at least 40%, at least 50%, at least 60%, at least 70% or at least 80% compared to a cell, plant, embryo, or cell of a subject with wild-type APC function.

APC activators include small molecules and biologics (for example, peptides, proteins, nucleic acids, antibodies).

The activator is optionally a direct or an indirect activator.

In one embodiment, the APC activator comprises a peptide comprising an amino acid sequence as shown in any one of SEQ ID NOs: 1-17 or a conservatively substituted variant thereof or any other peptide described herein. In a further embodiment, the activator is Mad2 Inhibitor-1 (M2I-1). M2I-1 is a commercially available APC activate that binds to MAD2 and disrupts the interaction between MAD2 and CDC20. The disruption of this interaction causes the APC to become activated earlier than usual.

As shown in FIG. 3, yeast protein histone H2A.Z (Htz1) is an APC activator. Accordingly, in another embodiment, the APC activator is (a) Htz1, (b) a fragment of Htz1 which has the same or similar APC activator activity as Htz1 (for example, increases the viability of a cell with defective APC function or activity and/or binds the APC), (c) a protein or fragment having at least 30, 40, 50, 60, 70, 80, 90, 95 or 99% sequence identity with (a) or (b), or (d) a conservatively substituted variant of (a) or (b). In one embodiment, Htz1 is *Saccharomyces cerevisae* Htz1. Sequences for Htz1, and the gene encoding Htz1 can be found, for example in online databases such as UniProt and GenBank.

Methods of Delaying Signs or Symptoms of Aging, Increasing Lifespan and/or Increasing Stress Resistance The APC activators disclosed herein increase the viability of a cell with defective anaphase promoting complex (APC) function and/or specifically bind the APC. The APC targets proteins that promote aging for degradation and is required for stress resistance and extended lifespan. Accordingly, the APC activators of the present disclosure are useful for delaying one or more symptoms of aging, increasing lifespan and/or increasing stress resistance in a cell including a microbial, plant or mammalian cell, in a plant or mammalian embryo or in a plant or subject.

The APC activators disclosed herein are particularly useful for increasing lifespan and/or increasing stress resistance in yeast cells. The yeast cells are optionally yeast cells used in industrial fermentation applications where increasing the lifespan and/or stress resistance of the yeast cells would be describable. For example, yeast is used for fermentation in the production of bread, wine and beer and also in the biofuel industry, to produce ethanol.

As used herein, the term "aging" refers to an age-dependent or age-progressive decline in intrinsic physiological function. The term "delaying one or more symptoms of aging" includes, but is not limited to, reversing, alleviating, preventing or inhibiting the progression of aging or symptoms or conditions associated with aging.

Signs and symptoms of aging in mammals such as humans include, but are not limited to, hearing loss, cognitive decline, wrinkles, fertility decline, hair greying, osteoarthritis, frailty, atherosclerosis, generalized organ atrophy, diminished stress tolerance and reduced longevity. The aging process is also manifested at the cellular level. Signs and symptoms of cellular aging include, but are not limited to, loss of doubling capacity, increased levels of apoptosis, changes in differentiated phenotype, and changes in metabolism, e.g., decreased levels of protein synthesis and turnover. Telomere shortening may also be an indicator of aging. Any of the signs and symptoms described above may be decreased by at least 5, 10, 25, 50, 75 or 100% compared to what would be expected without treatment without treatment with or expression of a an APC activator as described herein.

The length of time from birth to death is known as the life span of an organism, and each organism has a characteristic average life span. In addition, cells which are not capable of continuous growth in culture (non-immortal cells or cell lines) are characterized by a predictable lifespan in vitro, broadly divisible into three phases corresponding to growth, maturation, and decline (i.e., senescence). The life spans of many non-immortal cells in culture, particularly mammalian cells, frequently varies from only a matter of hours to only several weeks, even under optimal culture conditions. Even "immortal cells" tend to lose viability as a function of time in culture, with corresponding decline of the cell mass.

As used herein, the term "increasing longevity" includes extending lifespan. Lifespan is optionally extended by at least 1, 3 or 5 days, 1, 2, 3, 4, 5 or 6 weeks, 1, 2, 3, 6 or 12 months, or at least 2, 3, 4, 5 or 10 years over the lifespan that would be expected without treatment with or expression of an APC activator as described herein.

As used herein, the term "stress resistance" refers to the ability of a cell or organism to withstand external or internal stress. Examples of external stresses include environmental stresses include non-optimal temperature, pH, and/or nutrient availability (oxygen, water, salt, food). Environmental stresses also include exposure to toxic agents. In yeast cells, for example, $H_2O_2$ induces oxidative stress whereas galactose induces a carbon stress. In plants and plant cells, environmental stresses include drought and temperature.

In one embodiment, stress resistance is determined by measuring one or more well-known responses to stress. Responses to stress include increased expression of one or more genes or proteins known to be required for stress resistance.

For example, in yeast cells, the expression of Cin5, a transcription factor is induced under stress. Accordingly, a decrease in expression of Cin5 in yeast can be used to indicate stress resistance.

Stress resistance may be increased by at least 5, 10, 25, 50, 75 or 100% compared to what would be expected without treatment without treatment with or expression of an APC activator as described herein.

In one embodiment, the APC activators described herein are used in a method for delaying signs or symptoms of aging, increasing lifespan and/or increasing stress resistance, the method comprising administering an effective amount of a peptide or composition disclosed herein to an animal or cell in need thereof.

In another embodiment, an effective amount of an APC activator is used for delaying aging, increasing lifespan and/or increasing stress resistance. In another embodiment, a peptide or composition disclosed herein is used in the preparation of a medicament for delaying signs or symptoms of aging, increasing lifespan and/or increasing stress resistance.

In yet another embodiment, a use of an effective amount of an APC activator for delaying signs or symptoms of aging, increasing lifespan and/or increasing stress resistance is provided.

Where the APC activator is a peptide, "administering a peptide" includes both the administration of the peptide as well as the administration of a nucleic acid sequence encoding the peptide to an animal or to a cell in vitro or in vivo. The term "administering" also includes the administration of a cell that expresses the peptide. The peptides described herein may be administered in vivo or ex vivo to a cell which is then administered. For example, cells may be transformed or transduced with the nucleic acid encoding the peptide described herein and then the cells are administered in vivo.

In one embodiment, the APC activators are for use orally, topically or intravenously or are administered orally, topically or intravenously. In one particular embodiment, a peptide is for topical administration to a plant.

An effective amount of an APC activator of the disclosure relates generally to the amount needed to achieve a desired objective, for example, modulating APC activity. In one embodiment, an APC activator is administered to a cell or subject where APC levels are low and/or the activity of the APC is impaired.

The amount required to be administered will furthermore depend on the activity of the APC activator, and will also depend on the rate at which an administered peptide is depleted from the free volume of the subject to which it is administered. Common ranges for effective dosing of a peptide of the disclosure may be, by way of non-limiting example, from about 0.1 mg kg body weight to about 50 mg/kg body weight. Common dosing frequencies may range, for example, from twice daily to once a week.

Efficaciousness of treatment can be determined in association with any known method for assaying delayed signs or symptoms of aging, increased lifespan and/or increased stress resistance.

In one embodiment, the APC activator may be used in combination with at least one additional agent. Accordingly, the disclosure provides a method for delaying signs or symptoms of aging, increasing lifespan and/or increasing stress resistance using an APC activator in combination with at least one additional agent. An additional agent may be administered prior to, overlapping with, concurrently, and/or after administration of the active ingredients. When administered concurrently, an APC activator and an additional agent may be administered in a single formulation or in separate formulations, and if administered separately, then optionally, by different modes of administration. The combination of APC activators and one or more other agents may synergistically act to combat signs or symptoms or aging or stress or increase lifespan.

Methods of Treating Cancer

The present disclosure shows that an activator of the Anaphase Promoting Complex (APC) (M2I-1), reduced the levels of APC substrates in drug-resistant breast cancer cells in culture, sensitized cancer cells to a chemotherapeutic and stalled tumour growth in mouse model of triple negative breast cancer.

Accordingly, the disclosure also provides a use of an activator of the Anaphase Promoting Complex (APC) for sensitizing cancer cells and/or treating cancer in a subject in need thereof. Also provided is a method of sensitizing cancer cells and/or treating cancer in a subject in need thereof by administering an activator of the Anaphase Promoting Complex (APC) to the subject. In another embodiment, an effective amount of the activator is used for treating cancer in a subject in need thereof. In another embodiment, the activator is used in the preparation of a medicament for cancer in a subject in need thereof.

In one embodiment, the cancer is an aggressive cancer.

In one embodiment, the cancer is breast cancer, optionally ER+ breast cancer, ER/PR+ breast cancer, HER2+ breast or "triple negative breast cancer" (ER/PR-HER2− breast cancer). In another embodiment, the cancer is lymphoma, optionally Hodgkin or non-Hodgkin lymphoma.

As described herein, it is demonstrated drug resistant breast cancer cells and dog lymphoma cells selected for drug resistance were treated with chemotherapy, only those cells in the presence of M2I-1 were killed. In addition, tumour growth in a mouse model with doxorubicin triple negative breast cancer was decreased following administration of M2I-1. Thus, in one embodiment, the cancer is a drug resistant cancer, for example a drug resistant breast cancer or lymphoma. Examples of drugs for which resistance can develop in cancer cells include, but are not limited to, doxorubicin, capecitabine, carboplatin, cyclophosphamide, gemcitabine, paclitaxel and vinorelbine.

As used herein, the phrase "treating cancer" refers to inhibiting of cancer cell replication, preventing transformation of a cell to a cancer-forming cell, inhibiting of cancer spread (metastasis), inhibiting of tumor growth, reducing cancer cell number or tumor growth, decreasing in the malignant grade of a cancer (e.g., increased differentiation), or improving cancer-related symptoms.

An effective amount of an activator of the disclosure relates generally to the amount needed to achieve a desired objective, for example, modulating APC activity. In one embodiment, an activator is administered to a cell or subject where APC levels are low and/or the activity of the APC is impaired.

The amount required to be administered will furthermore depend on the activity of the activator, and will also depend on the rate at which an administered activator is depleted from the free volume of the subject to which it is administered. Common ranges for effective dosing of an activator of the disclosure may be, by way of non-limiting example, from about 0.1 mg kg body weight to about 50 mg/kg body weight. Common dosing frequencies may range, for example, from twice daily to once a week.

Efficaciousness of treatment can be determined in association with any known method for determining the effectiveness of a cancer treatment.

Further, the activator may be used in combination with at least one additional agent for treating cancer. The additional agent is optionally a therapeutic drug, for example a chemotherapeutic. In one embodiment, the additional agent is a chemotherapeutic used to treat breast cancer. Chemotherapeutic agents used to treat breast cancer include, but are not limited to, capecitabine, carboplatin, cyclophosphamide, doxorubicin, gemcitabine, paclitaxel and vinorelbine. In another embodiment, the additional agent is a chemotherapeutic used to treat lymphoma.

Accordingly, the disclosure provides a method for treating cancer using an APC activator in combination with at least one additional agent. An additional agent may be administered prior to, overlapping with, concurrently, and/or after administration of the activator. In one embodiment, the APC activator and the additional agent are administered contemporaneously as part of a regimen. When administered concurrently, the activator and an additional agent may be administered in a single formulation or in separate formulations, and if administered separately, then optionally, by different modes of administration.

Also provided is a method of sensitizing cancer cells to a chemotherapeutic, the method comprising administering an APC activator in combination with a chemotherapeutic in a subject in need thereof. In one embodiment, the subject in need thereof is a subject with a chemotherapeutic-resistance cancer.

Methods of Increasing Stress Resistance

The present disclosure also shows that the expression of peptide C43-4 into wheat embryos results in increased germination of the transformed embryos and reduced levels of APC substrates.

Accordingly, the present disclosure also provides a method of increasing the stress resistance of a mammalian cell, plant or plant cell, the method comprising:
 (a) introducing a nucleic acid molecule encoding a peptide as described herein into a mammalian cell, plant or plant cell and
 (b) growing the mammalian cell, plant or plant cell to obtain a mammalian cell, plant or plant cell that expresses the peptide.

Also provided herein is a recombinant plant or plant cell, wherein the plant or plant cell expresses a peptide as described herein. In one embodiment, the recombinant plant has a faster germination rate, increased stress resistance, increased longevity and/or increased hardiness compared to a corresponding non-recombinant plant. Each of these measures may be increased by at least 5, 10, 25, 50, 75 or 100% compared to a corresponding non-recombinant plant.

Further provided is a recombinant mammalian cell, wherein the mammalian cell expresses a peptide as described herein and the mammalian cell has increased stress resistant compared to a corresponding, non-recombinant mammalian cell. Stress resistance may be increased by at least 5, 10, 25, 50, 75 or 100% compared to a corresponding non-recombinant mammalian cell.

As described above, also provided herein are plant vectors comprising a nucleic acid encoding a peptide as described herein. As used herein, the term "plant vector" means a nucleic acid molecule, such as a plasmid, comprising regulatory elements and a site for introducing transgenic DNA, which is used to introduce said transgenic DNA into a plant.

The phrase "introducing a nucleic acid molecule into" includes both the stable integration of the nucleic acid molecule into the genome of for example a plant, plant cell or mammalian cell as well as the transient integration of the nucleic acid into a plant, plant cell or mammalian cell. Accordingly, the recombinant plant cell or mammalian cell may express the encoded peptide in a stable or transient manner.

As used herein, the term "plant" includes a plant cell and a plant part. The term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like.

The phrase "growing a plant or plant cell to obtain a plant that expresses peptide" includes both growing recombinant plant cells into a mature plant as well as growing or culturing a mature plant that has received the nucleic acid molecules encoding the peptide. One of skill in the art can readily determine the appropriate growth conditions in each case.

The term "plant" refers to any organism of the kingdom Plantae. In one embodiment, the plant is a crop, for example a grain crop such as wheat, rapeseed, alfalfa, barley, canola, flax, rye, and oats, a vegetable crop, a fruit crop or a tobacco crop. In another embodiment, the plant is *Arapidopsis*.

The nucleic acid molecule or vector containing the nucleic acid molecule may be introduced into the plant using techniques known in the art including, without limitation, electroporation, an accelerated particle delivery method (biolistic method), a cell fusion method or by any other method to deliver the nucleic acid to a plant or plant cell, including *Agrobacterium* mediated delivery, or other bacterial delivery such as *Rhizobium* sp. NGR234, *Sinorhizobium meliloti* and *Mesorhizobium loti* (Chung et al., 2006). In another embodiment, the nucleic acid molecule or vector containing the nucleic acid molecule may be introduced into the plant by the "floral-spray" or "floral-dip" method. For example, in the floral-spray or floral dip method, a plant or plant part is contacted with a bacterial vector delivery system by spray or dip. In one embodiment, a plant (for example, the influoresces or leaves of the plant) is sprayed with a composition comprising an *Agrobacterium* transformed with a nucleic acid molecule or vector of interest and then grown under normal growing conditions.

After selection of peptide expressing primary transgenic plants, or concurrent with selection of peptide expressing plants, derivation of homozygous stable transgenic plant lines may be performed. Primary transgenic plants may be grown to maturity, allowed to self-pollinate, and produce seed.

Methods of introducing a nucleic acid molecule encoding a peptide of interest to a mammalian cell are known in the art. For example, various methods of transfection are known including, but not limited to, chemical transfection, non-chemical transfection (for example, electroporation), particle-based methods, viral methods, and combinations thereof. Transfection may result in a stable or transiently transfected recombinant cell.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Yeast forward- and reverse-genetic screens were performed to identify small peptides that impact APC function. By definition, a reverse screen can discover the function of a gene using gene/protein specific tools, whereas a forward screen can uncover the genetic basis of a phenotype.

The reverse genetic screen utilized a yeast 2-hybrid (Y2H) protocol that selected for peptides that bound to the APC subunits Apc5 or Apc10 (see FIG. 5 for APC structure), to assess whether peptide-binding might modify APC function. Peptides that bound APC subunits were then assayed for those that suppressed APC mutant defects.

A library of random small peptides were cloned into a Thioredoxin (Trx) scaffold (see FIG. 6 for Trx-aptamer structure) and expressed from a galactose-inducible Y2H prey vector in cells expressing the Apc10 bait vector (the modified Apc10 is still part of the complete APC complex). Six peptides that reproducibly interacted with the Apc10 bait construct in Y2H assays were identified (FIG. 1A) and were examined further.

Figure 1B:
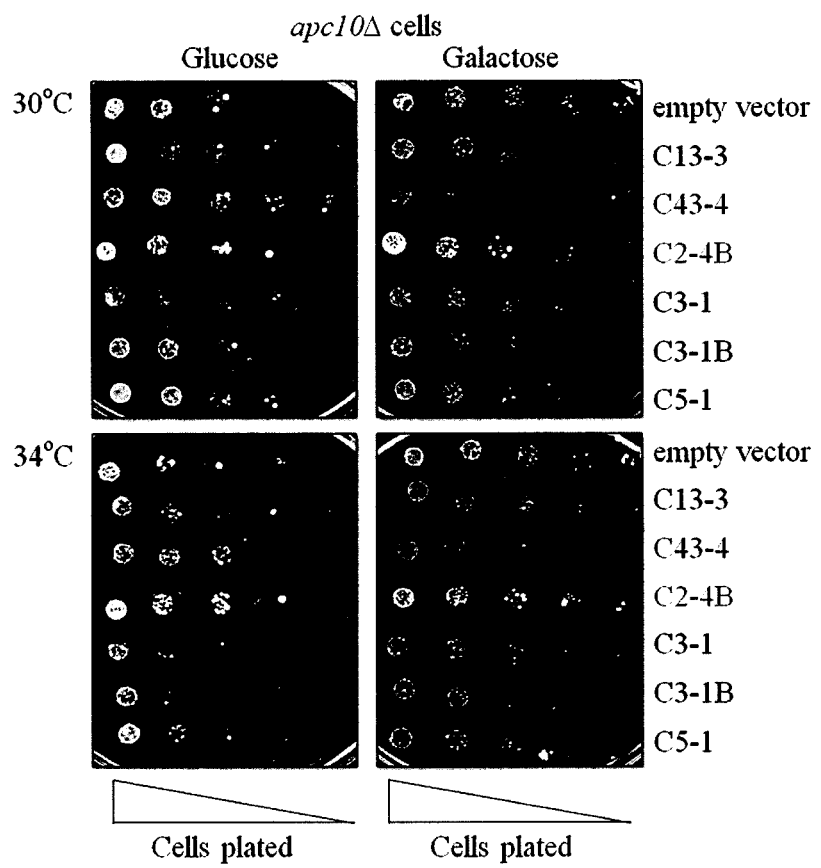
Figure 1C:
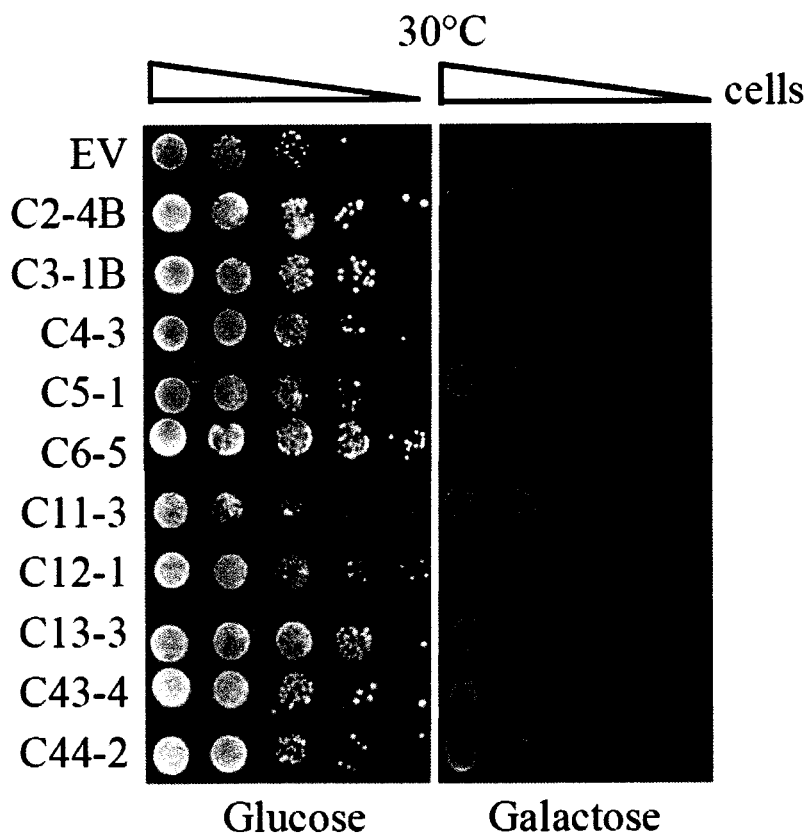
Figure 1D:
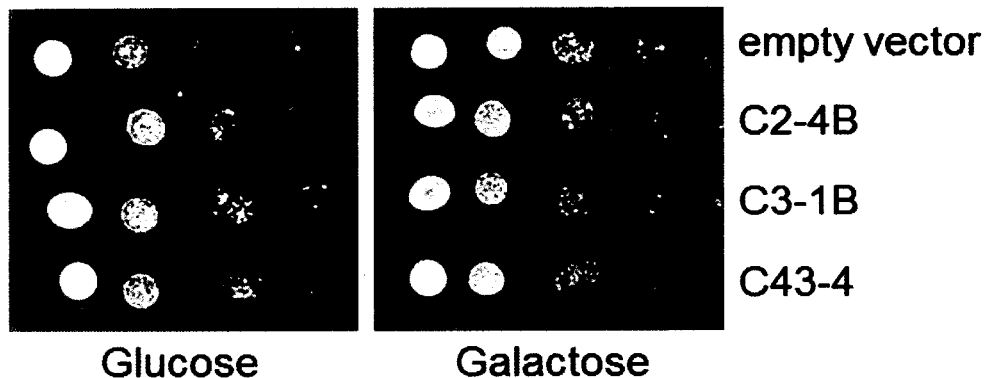
Figure 2A:
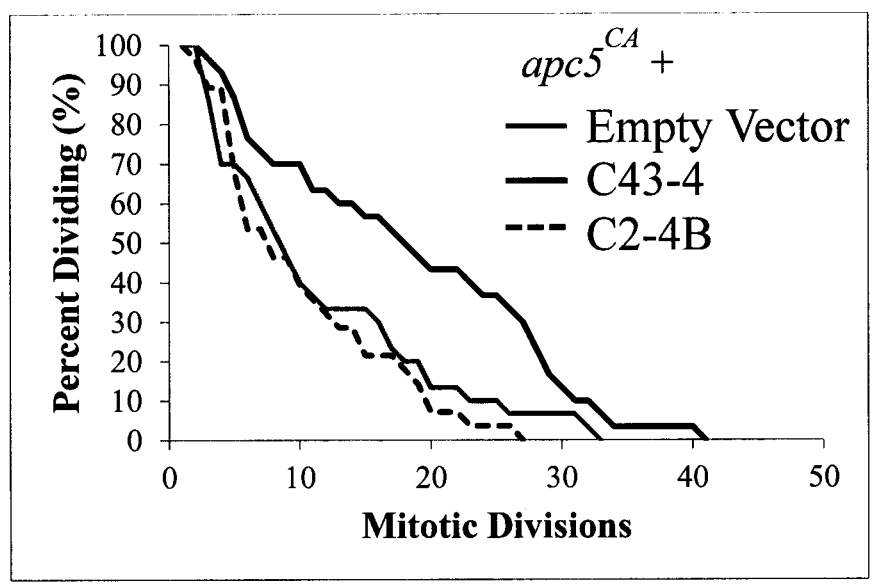
Figure 2B:
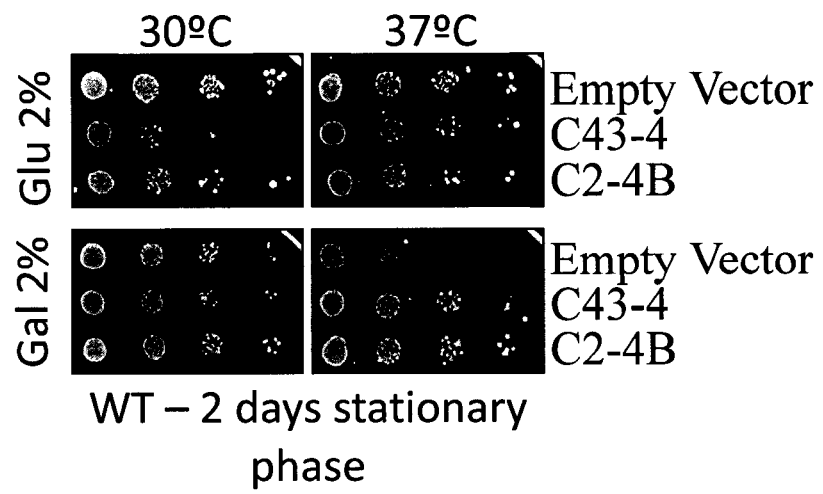

The six peptide expressing vectors were transformed into apc10Δ cells and assessed for temperature sensitive growth. Two of the peptides, C43-4 and C2-4B, suppressed the apc10Δ growth phenotype at 30 and 34° C. (FIG. 1B-D). Neither C43-4 nor C2-4B influenced log phase growth of wild type (WT) cells at 30° C. However, C43-4 and C2-4B increased replicative and chronological lifespan in both apc5$^{CA}$ and WT cells, respectively (FIG. 2A). In addition, when C43-4 and C2-4B were overexpressed in WT yeast cells, increased stress resistance (FIG. 2B) was observed. $H_2O_2$ induces oxidative stress whereas galactose induces a carbon stress.

Sequencing of C43-4 and C2-4B revealed that C43-4 shared sequence homology with Htz1, while C2-4B was similar to Sum1 (FIGS. 7, 8). C43-4 is 20 residues long, with a 13 amino acid stretch sharing 46% identity and 85% similarity with a 13 residue region in Htz1, defining a motif of potential significance. Htz1 is a histone H2A variant that responds to DNA damage by recruiting Gcn5, a histone acetyltransferase, to promoters to acetylate histones and increase transcription (Yu et al, 2013). Apc5 and Gcn5 interact to promote H3 acetylation during mitosis (Turner et al, 2010). It is shown here that overexpression of GST-HTZ1 in APC mutants suppressed temperature sensitive (ts) growth and sensitivity to $H_2O_2$ (FIG. 3) and, in WT cells, caused increased Apc10 protein accumulation, while it accumulated and was stabilized in APC mutants (FIG. 10). Previous work showed that increased Apc10 in cells prolonged replicative lifespan (Harkness et al. 2004). Without being bound by theory, this could reflect an interaction between Gcn5 and Htz1 that elevates APC activity by increasing APC subunit levels under stress conditions. In conclusion, the small peptides C43-4 and C2-4B suppressed APC defects, increased stress resistance, and enhanced lifespan.

Using a forward genetic screen to test whether temperature sensitive (ts) APC mutants expressing random small peptides could grow at restrictive temperatures, millions of small peptides were rapidly screened for those that could restore mutant APC phenotypes. Peptides that rescued the apc5$^{CA}$ ts (temperature sensitive) defect were recovered including peptides Y65 and Y36.

One peptide in particular, Y65, was of interest because it had homology to Elongin C (Elc1; Y65 is 20 amino acids in length, with a 7 residue stretch sharing 86% identity and 100% similarity with Elc1). Elc1 is a ubiquitin-protein ligase (E3) conserved among eukaryotes that is involved in DNA repair (Harreman et al, 2009; Ribar et al, 2007). To identify what the peptides bound in order to modify APC activity, Y65 was cloned into the Y2H bait vector and used to identify binding partners. One peptide binding partner was isolated, Cin5, a transcription factor that is induced when stressed.

Figure 4A:
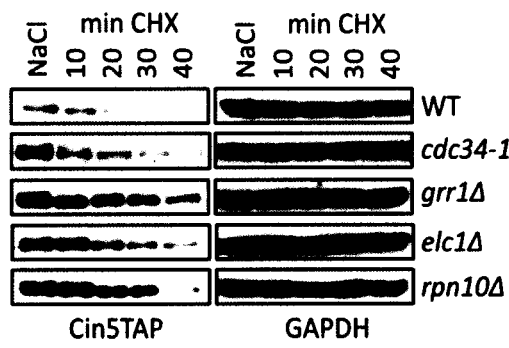
Figure 4B:
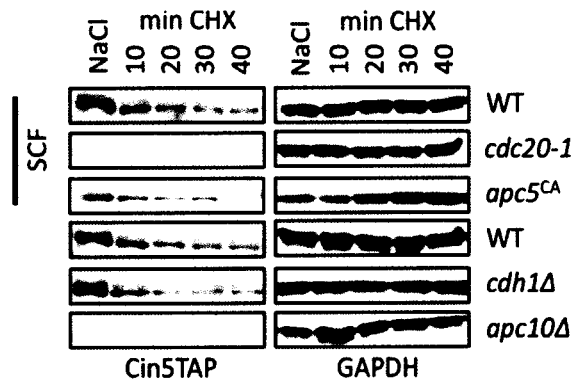

It was observed that Cin5 protein is at low levels and unstable under normal conditions, but accumulated upon a variety of stresses, as observed by others (Nevitt et al, 2004). Cin5 degradation depends on the proteasome, as it is stable in the proteasome mutant rpn10Δ (FIG. 4A). It was found that mutations to the SCF (Skp/Cullin/F-Box) E3, which works in opposition to the APC, stabilized Cin5 (FIG. 4A), whereas mutations that impair APC mitotic function (cdc20-1), but not G1 function (cdh1Δ), cause further Cin5 degradation (FIG. 4B). Thus, without being bound by theory, the ubiquitin pathway (APC and SCF; FIG. 4) appears to play a complex role in Cin5 stability, allowing flexible adaptation to stress.

Methodology

Random small peptides were cloned into the TrxA scaffold (library provided by R. Geyer, U of S) and expressed from a galactose-inducible Y2H prey vector in cells harboring either APC5 or APC10 Y2H bait vectors (APC5/APC10 bait constructs complement APC mutant defects).

Over 100 peptides that bound either Apc5 or Apc10 were recovered from millions screened. Six peptides that reproducibly interacted with the Apc10 bait construct in Y2H assays were examined further. Vectors expressing these 6 peptides were transformed into APC mutant cells and assessed for ts growth.

In the forward screens, with galactose-inducible TrxA-based peptide libraries, in cells harboring the apc5$^{CA}$ ts allele, over 200 peptides (from millions screened) suppressed the ts phenotype. Several recovered plasmids were sequenced.

Example 2

As described in Example 1 above, small peptides have been identified that bind the APC and/or suppress APC mutants. These peptides increase longevity and make yeast cells more resistant to stressors. In particular, a small peptide with a protein sequence similar to that of histone protein Htz1 that increased longevity and resistance to stress was identified (C43-4).

Residues 2, 7, 8, 10, 12 and 14 of peptide C43-4 are conserved with Htz1. All of these residues were mutated to alanine (FIG. 11). Peptides that contained mutations designed to determine which amino acids were required for function were generated. These mutant peptides were grown in wild type cells and in cells that had APC5 and APC10 mutated, under temperature and UV stress conditions.

Results

Galactose inducible C43-4 peptides, that had been mutated at 6 amino acids that are conserved with Htz1, were expressed in wild type (WT) cells. The mutated sequences set out below:

| Mutant | Alternative reference | Description | Sequence | SEQ ID NO: |
|---|---|---|---|---|
| C43-4-1 | C43-G2A | alanine at position 2 of C43-4 | NASSHNDL RVRRLTLI SRLC | 18 |
| C43-4-2 | C43-D7A | alanine at position 7 of C43-4 | NGSSHNAL RVRRLTLI SRLC | 19 |
| C43-4-3 | C43-L8A | alanine at position 8 of C43-4 | NGSSHNDA RVRRLTLI SRLC | 20 |
| C43-4-4 | C43-V10A | alanine at position 10 of C43-4 | NGSSHNDL RARRLTLI SRLC | 21 |
| C43-4-5 | C43-R12A | alanine at position 12 of C43-4 | NGSSHNDL RVRALTLI SRLC | 22 |
| C43-4-6 | C43-T14A | alanine at position 14 of C43-4 | NGSSHNDL RVRRLALI SRLC | 23 |

These cells were spot diluted on Trp-plates and grown at the temperatures shown and/or exposed to ultraviolet (UV) irradiation (FIG. 11). At low level expression on glucose, some of the mutations caused stress dependent phenotypes. The peptide at low levels required at least three different amino acids, as mutants C43-4-2, C43-4-5 and C43-4-6 were similar to the empty vector.

At low level expression, the WT peptide increased stress resistance. Mutant C43-4-3 increased stress resistance further, likely by increasing the activity of the peptide.

In addition, the peptide required wild-type amino acids at amino acid numbers 7, 12 and 14 for function.

FIG. 12 shows peptides expressed in WT cells and grown on galactose media to induce the peptides at the temperatures shown. The cells were exposed to 5 sec of UV from a UV box prior to incubation. The plus signs define growth compared to the empty vector control.

Expression of the WT and mutant peptides have reduced activity in apc10Δ cells (FIG. 13). Only the C43-4-3 mutant remained toxic in these cells, again consistent with increased activity of this mutant.

Methods
1. Cells were cultured overnight in Trp-2% glucose media
2. The growth of the cells was determined by measuring the optical density (OD) of the cells at 600 nm ($OD_{600}$)
3. Cells were diluted to $OD_{600}$ of 1 with fresh culture media
4. 100 ul of each culture was pipetted into a well of a 96 well plate
5. 10 ul of the each starting culture was pipetted into 90 ul of water in 4 additional wells to make a 10-fold serial spot dilution
6. 5 ul from each serial dilution was spotted onto plates containing standard growth media with either 2% glucose or 2% galactose using a multi-pipettor
7. The plates were exposed to UV
8. The plates were then placed at room temperature, 30, 34 or 37° C. for 3-7 days
9. The plates were scanned and saved as tiff files Example 3

Expression of C43-4 in Wheat Embryos

C43-4 was subcloned into a plant vector and expressed in wheat embryos.

The wheat embryos (scutella) were transformed using a Biolistics-mediated transformation of wheat embryos. Wheat embryos were inoculated with *Agrobacterium* harbouring an RFP expression vector. Following inoculation with *Agrobacterium*, embryos were placed on a medium that allows for growth of both the embryos and the *Agrobacterium*. Timentin was used for killing remaining *A. tumefaciens* cells after co-cultivation.

The peptide localized to the nucleus. The initial transformed embryos germinated faster. Germination rate was determined as a function of time to observe growth from the embryo and on average, the transformed embryos containing the peptide germinated before empty vector controls. In addition, a tested APC substrate in the embryo is at a reduced level indicating that APC activity is indeed increased (FIG. 14). Accordingly, the Htz1-like peptide (C43-4) activates the APC in plants.

APC targets APC substrates for degradation such that the relative levels provides an indication of APC activity in a cell. For example, if the substrates are reduced, without being bound by any theory, it is believed to mean that the APC is working better. The faster germination rate of the wheat embryos indicates that these embryos are healthier than the control embryos, a condition that increases lifespan.

Example 4

Activation of the APC Provides a Benefit to Cells

APC activator Mad2 Inhibitor-1 (M2I-1) is a small molecule that binds MAD2. MAD2 acts to inhibit APC function by sequestering away the APC activator CDC20. By disrupting the MAD2/CDC20 interaction, M2I-1 causes the APC to become activated earlier than usual.

Figure 15A:
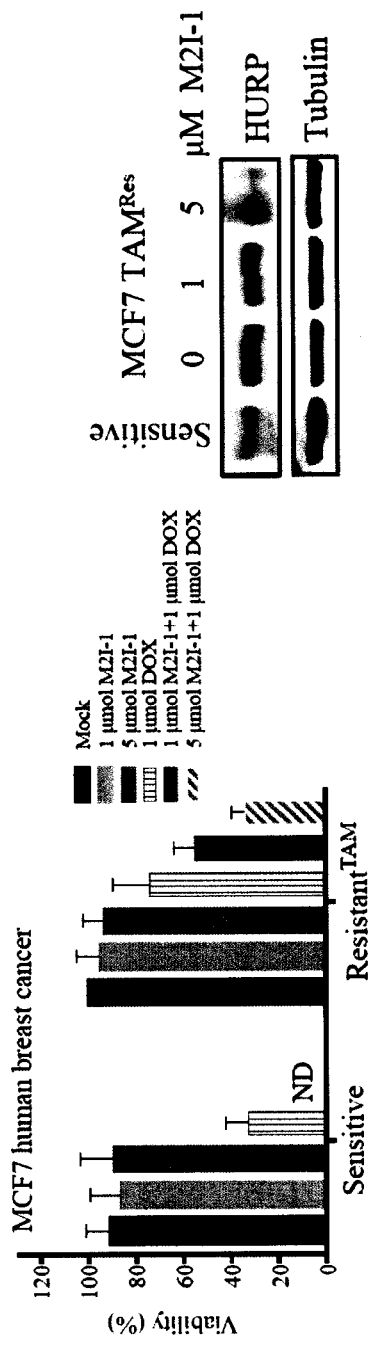
Figure 15B:
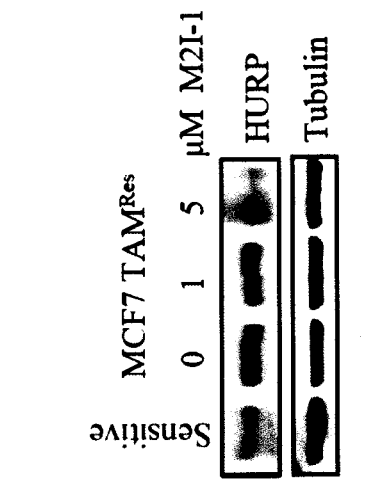
Figure 15C:
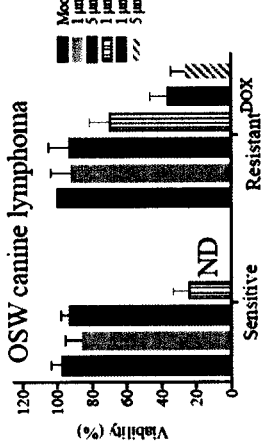
Figure 15D:
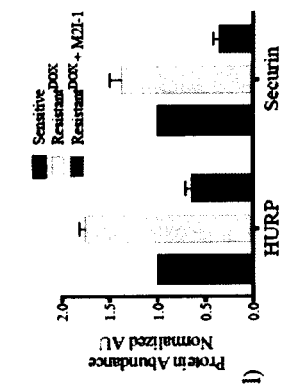
Figure 15E:

Drug resistant human breast cancer cells in culture were treated with the M2I-1 activator. M2I-1 did not impair the growth of these cells alone (FIG. 15A), but reduced the levels of several APC substrates tested (FIG. 15B), showing that the APC was activated. When chemotherapy was used with or without M2I-1, only in the presence of M2I-1 were cells killed (FIG. 15A). This was observed in drug resistant cells generated from both human MCF7 breast cancer cells (FIGS. 15A and 15B) and in OSW dog lymphoma cells (FIGS. 15C-E) selected for drug resistance. Without being bound by theory, these results suggest that activating the APC may be a general mechanism of protecting against drug resistance and not cell line or species specific.

A mouse model for growing patient derived breast tumor cells obtained from a patient with triple negative breast cancer was developed. This patient had developed resistance to Doxorubicin. Tumors growing in these mice grow rapidly. A mouse was injected with 25 mg/kg M2I-1. It was observed that tumor growth was stalled in these cells and markers of APC substrates were positive for APC activation in the tumor (FIG. 16).

Without being bound by theory, reduced APC activity may be associated with aggressive cancers, while increased APC activity appears to sensitize cancer cells, both in vitro and in vivo, to chemotherapy.

List of Peptides

TABLE 1

The peptides listed below (a) increase the viability of an apc5$^{temperature\ sensitive}$ mutant and/or an apc10Δ mutant and (b) bind the APC.

| Peptide sequence | | SEQ ID NO: | Notes |
|---|---|---|---|
| NGSSHNDL RVRRLTLI SRLC | C43-4 | 1 | Binds Apc10<br>Residues 2-14 (GSSHNDLRVRRLT; SEQ ID NO: 12) overlap with Hzt1 in yeast. Various degrees of similarity to Htz1, Cst9, Rpt1 (proteasome), Svf1 (survival pathway), Elm1 (Snf1 kinase) and Ddc1 were determined using a BLAST search. |
| NGSSHNDA RVRRLTLI SRLC | C43-4-3; C43-L8A | 2 | Version of C43-4 where the leucine residue at position 8 is replaced with alanine<br>The following motif was identified in several different peptide sequences: SSH |
| CECLETET FHPITRHL IVPV | 9-5 | 3 | Residues 5-19 (ETETFHPITRHLIVP; SEQ ID NO: 13) overlap with Swe1 in yeast/Wee1 in humans<br>Binds Apc5<br>Interacts with Die2, Tim44, Yrm1 and Scp160 in a yeast 2 hybrid assay |
| RMPQWWQW MWV | C2-4B; 11-3 | 4 | Has homology with yeast protein Sum 1.<br>Residues 1-9 (RMPQWWQWM; SEQ ID NO: 14) overlap with Naf1 in yeast/NAF1 in humans. Naf1/NAF1 is involved in pre-rRNA processing<br>Binds Apc5<br>Identified as interacting with Sum1, Vas1, Shh3, Dbr1 in a yeast 2 hybrid assay |
| PSYNTIKY HETHGGRH PRRQPKRP I | 3-1 | 5 | Residues 16-25 (HPRRQPKRPI; SEQ ID NO: 15) overlap with Rrp9 in yeast/RRP9 in humans. Rrp9 is involved in pre-rRNA processing<br>Residues 15-21 (THGGRHP; SEQ ID NO: 16) overlap with Hos2 in yeast/HOS2 in humans. Hos2 is a histone acetyltranferase/HOS2 in humans<br>Residues 2-21 (SYNTIKYHETHGGRHPRRQP; SEQ ID NO: 17) overlap with Hap1 in yeast. Hap1 is required for caloric restriction, heme activator<br>Binds Apc10<br>Identified as interacting with Sld5, Hms2, Gnt1 and Vnx1 in a yeast 2-hybrid assay<br>The following motif was identified in several different peptide sequences: PRR |

TABLE 1-continued

The peptides listed below (a) increase the viability of an apc5$^{temperature\ sensitive}$ mutant and/or an apc10Δ mutant and (b) bind the APC.

| Peptide sequence | | SEQ ID NO: | Notes |
|---|---|---|---|
| GALKEVCI CIVESVGG EVFSGP | 4 | 6 | Has homology with yeast proteins Mad2, Hxt2, Ubc7<br>Binds Apc5<br>Identified as interacting with Hxt2, Mad2, Ubc7, Rpp2, Kap122, Sfa1, Oac1 and Vps13 in a yeast 2-hybrid assay |
| SKWTWRMC MSWTVDRF APVPWP | 24-1 | 7 | Binds Apc5<br>Identified as interacting with Nup82, Scs3, Syf1 and Kap104 in a yeast 2-hybrid assay<br>The following motifs were identified in several different peptide sequences: SKWT and MCMS |
| GRMLMTYL MYFMVLWV PRPWGPPL | 1-8 | 8 | Binds Apc10<br>The following motifs were identified in several different peptide sequences: PRP and PPL |
| RRCLSIRT ENLAWEGK FLRV | 50-1 | 9 | Binds Apc10<br>Identified as interacting with Pxa1, Rrp12, and Hfm1 in a yeast 2-hybrid assay |

TABLE 2

The peptides listed below increase the viability of an apc5$^{temperature\ sensitive}$ mutant

| Peptide sequence | | SEQ ID NO: | Notes |
|---|---|---|---|
| VRQKSDKE YERVLGLG LRRL | Y65 | 10 | Rescues apc5$^{CA}$ temperature sensitive (ts) growth but does not bind the APC in a yeast 2HY assay<br>Has homology with yeast protein Elc1 as well as Spc110 (cohesion complex), Cbs2, Stb2 and Tfb3<br>Interacts with Cin5 in a yeast 2 hybrid assay |
| SWLNGSGG VVLWLFSN FCCG | Y36 | 11 | Rescues apc5$^{CA}$ temperature sensitive (ts) growth but does not bind the APC in a yeast 2HY assay |

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety.

REFERENCES

Harkness T A, Shea K A, Legrand C, Brahmania M, Davies G F. (2004). A functional analysis reveals dependence on the anaphase-promoting complex for prolonged life span in yeast. Genetics 168:759-74.

Postnikoff S D, Harkness T A. (2014). Replicative and chronological life-span assays. Methods Mol Biol 1163: 223-7.

Postnikoff S D, Malo M E, Wong B, Harkness T A. (2012). The yeast forkhead transcription factors fkh1 and fkh2 regulate lifespan and stress response together with the anaphase-promoting complex. PLoS Genet 8:e1002583.

Menzel J, Malo M E, Chan C, Prusinkiewicz M, Arnason T G, Harkness T A. (2014). The anaphase promoting complex regulates yeast lifespan and rDNA stability by targeting Fob1 for degradation. Genetics 196:693-709.

Harkness T A, Davies G F, Ramaswamy V, Arnason T G. (2002). The ubiquitin-dependent targeting pathway in Saccharomyces cerevisiae plays a critical role in multiple chromatin assembly regulatory steps. Genetics 162:615-32.

Harkness T A, Arnason T G, Legrand C, Pisclevich M G, Davies G F, Turner E L. (2005). Contribution of CAF-I to anaphase-promoting-complex-mediated mitotic chromatin assembly in Saccharomyces cerevisiae. Eukaryot Cell 4:673-84.

Turner E L, Malo M E, Pisclevich M G, Dash M D, Davies G F, et al. (2010). The Saccharomyces cerevisiae anaphase-promoting complex interacts with multiple histone-modifying enzymes to regulate cell cycle progression. Eukaryot Cell 9:1418-31.

Islam A, Turner E L, Menzel J, Malo M E, Harkness T A. (2011). Antagonistic Gcn5-Hda1 interactions revealed by mutations to the Anaphase Promoting Complex in yeast. Cell Div 6:13.

Jiao R, Postnikoff S, Harkness T A, Arnason T G. (2015). The SNF1 Kinase Ubiquitin-associated Domain Restrains Its Activation, Activity, and the Yeast Life Span. J Biol Chem 290:15393-404.

Malo M E, Postnikoff S D, Arnason T G, Harkness T A. (2016). Mitotic degradation of yeast Fkh1 by the Anaphase Promoting Complex is required for normal longevity, genomic stability and stress resistance. Aging 8:810-30.

Feser J, Truong D, Das C, Carson J J, Kieft J, et al. (2010). Elevated histone expression promotes life span extension. Mol Cell 39:724-35.

Yu Y, Deng Y, Reed S H, Millar C B, Waters R. (2013). Histone variant Htz1 promotes histone H3 acetylation to enhance nucleotide excision repair in Htz1 nucleosomes. Nucleic Acids Res 41:9006-19.

Millar C B, Xu F, Zhang K, Grunstein M. (2006). Acetylation of H2AZ Lys 14 is associated with genome-wide gene activity in yeast. Genes Dev 20:711-22.

Harreman M, Taschner M, Sigurdsson S, Anindya R, Reid J, et al. (2009). Distinct ubiquitin ligases act sequentially for RNA polymerase II polyubiquitylation. PNAS 106: 20705-10.

Ribar B, Prakash L, Prakash S. (2007). ELA1 and CUL3 are required along with ELC1 for RNA polymerase II polyubiquitylation and degradation in DNA-damaged yeast cells. MCB 27:3211-6.

Hanlon S E, Rizzo J M, Tatomer D C, Lieb J D, Buck M J. (2011). The stress response factors Yap6, Cin5, Phd1, and Skn7 direct targeting of the conserved co-repressor Tup1-Ssn6 in *S. cerevisiae*. PLoS One 6:e19060.

Furuchi T, Ishikawa H, Miura N, Ishizuka M, Kajiya K, et al. (2001). Two nuclear proteins, Cin5 and Ydr259c, confer resistance to cisplatin in *Saccharomyces cerevisiae*. Mol Pharmacol 59(3):470-4.

Jackson T, Kwon E, Chachulska A M, Hyman L E. (2000). Novel roles for elongin C in yeast. Biochim Biophys Acta 1491:161-76.

Nevitt T, Pereira J, Rodrigues-Pousada C. (2004). YAP4 gene expression is induced in response to several forms of stress in *Saccharomyces cerevisiae*. Yeast 21:1365-74.

Thornton B R, Ng T M, Matyskiela M E, Carroll C W, Morgan D O, Toczyski D P (2006) An architectural map of the anaphase-promoting complex. Genes Dev 20: 449-460.

The invention claimed is:

1. A peptide comprising
   amino acid sequence GSSHNDARVRRLT (SEQ ID NO: 34),
   wherein the peptide has a maximum length of 30 amino acids.

2. The peptide of claim 1, wherein the peptide consists of the amino acid sequence GSSHNDARVRRLT (SEQ ID NO: 34).

3. A compound comprising the peptide of claim 1 and an enhancer moiety, optionally wherein the enhancer moiety is a permeability enhancer, stability enhancer or bioavailability enhancer.

4. A composition comprising the peptide of claim 1 and a carrier.

5. A composition comprising at least two peptides according to claim 1.

6. A nucleic acid encoding the peptide of claim 1 or a vector comprising a nucleic acid encoding the peptide of claim 1.

7. A recombinant plant, microbial or mammalian cell, plant or mammalian embryo, plant or mammal that expresses:
   a. a peptide wherein the peptide comprises the peptide of claim 1;
   b. a compound comprising the peptide of claim 1 and an enhancer moiety, wherein the enhancer moiety is a carrier protein;
   c. a nucleic acid encoding the peptide of claim 1; or
   d. a vector comprising a nucleic acid encoding the peptide of claim 1.

8. The recombinant plant cell, plant embryo or plant of claim 7, wherein the plant is a crop, optionally wheat.

9. The recombinant plant or plant cell of claim 7, wherein the recombinant plant or plant cell has one or more of faster germination rate, increased stress resistance, increased longevity and/or increased hardiness compared to a plant or plant cell not expressing the peptide or compound.

10. A method of increasing resistance to stress and/or increasing lifespan in a plant, mammalian or microbial cell, in a plant or mammalian embryo or in a plant or subject, the method comprising administering a peptide comprising amino acid sequence GSSHNDARVRRLT (SEQ ID NO: 34) to the plant, mammalian or microbial cell, the plant or mammalian embryo or the plant or the subject, wherein the peptide has a maximum length of 30 amino acids.

11. The method of claim 10, wherein the peptide consists of GSSHNDARVRRLT (SEQ ID NO: 34).

12. The method of claim 10, wherein the peptide is conjugated to an enhancer moiety.

13. The method of claim 10, wherein the plant cell, embryo or plant is a crop cell, embryo or plant, optionally a wheat cell, embryo or plant.

14. A method of increasing the germination rate, stress resistance, longevity and/or hardiness of a plant or plant cell, the method comprising:
   a. introducing a nucleic acid molecule encoding the peptide of claim 1 into a plant or plant cell; and
   b. growing the plant or plant cell to obtain a recombinant plant or plant cell that expresses the peptide.

15. The method of claim 14, wherein the plant is a crop, optionally wheat.

* * * * *

SEQUENCE LISTING

```
<160> NUMBER OF SEQ ID NOS: 41

<210> SEQ ID NO 1
<211> LENGTH: 20
<212> TYPE: PRT
<213> ORGANISM: Artificial Sequence
<220> FEATURE:
<223> OTHER INFORMATION: Synthetic Construct

<400> SEQUENCE: 1

Asn Gly Ser Ser His Asn Asp Leu Arg Val Arg Arg Leu Thr Leu Ile
1               5                   10                  15

Ser Arg Leu Cys
            20

<210> SEQ ID NO 2
<211> LENGTH: 20
<212> TYPE: PRT
<213> ORGANISM: Artificial Sequene
<220> FEATURE:
<223> OTHER INFORMATION: Synthetic Construct

<400> SEQUENCE: 2

Asn Gly Ser Ser His Asn Asp Ala Arg Val Arg Arg Leu Thr Leu Ile
1               5                   10                  15

Ser Arg Leu Cys
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Construct

<400> SEQUENCE: 3

Cys Glu Cys Leu Glu Thr Glu Thr Phe His Pro Ile Thr Arg His Leu
1               5                   10                  15

Ile Val Pro Val
            20
```

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Arg Met Pro Gln Trp Trp Gln Trp Met Trp Val
1               5                   10

<210> SEQ ID NO 5
<211> LENGTH: 25
<212> TYPE: PRT
<213> ORGANISM: Artificial Sequence
<220> FEATURE:
<223> OTHER INFORMATION: Synthetic Construct

<400> SEQUENCE: 5

Pro Ser Tyr Asn Thr Ile Lys Tyr His Glu Thr His Gly Gly Arg His
1               5                   10                  15

Pro Arg Arg Gln Pro Lys Arg Pro Ile
            20                  25

<210> SEQ ID NO 6
<211> LENGTH: 22
<212> TYPE: PRT
<213> ORGANISM: Artificial Sequence
<220> FEATURE:
<223> OTHER INFORMATION: Synthetic Construct

<400> SEQUENCE: 6

Gly Ala Leu Lys Glu Val Cys Ile Cys Ile Val Glu Ser Val Gly Gly
1               5                   10                  15

Glu Val Phe Ser Gly Pro
            20

<210> SEQ ID NO 7
<211> LENGTH: 22
<212> TYPE: PRT
<213> ORGANISM: Artificial Sequence
<220> FEATURE:
<223> OTHER INFORMATION: Synthetic construct

<400> SEQUENCE: 7

Ser Lys Trp Thr Trp Arg Met Cys Met Ser Trp Thr Val Asp Arg Phe
1               5                   10                  15

Ala Pro Val Pro Trp Pro
            20

<210> SEQ ID NO 8
<211> LENGTH: 24
<212> TYPE: PRT
<213> ORGANISM: Artificial Sequence
<220> FEATURE:
<223> OTHER INFORMATION: Synthetic Construct

<400> SEQUENCE: 8

Gly Arg Met Leu Met Thr Tyr Leu Met Tyr Phe Met Val Leu Trp Val
1               5                   10                  15

Pro Arg Pro Trp Gly Pro Pro Leu
            20

```
<210> SEQ ID NO 9
<211> LENGTH: 20
<212> TYPE: PRT
<213> ORGANISM: Artificial Sequence
<220> FEATURE:
<223> OTHER INFORMATION: Synthetic Construct

<400> SEQUENCE: 9

Arg Arg Cys Leu Ser Ile Arg Thr Glu Asn Leu Ala Trp Glu Gly Lys
1               5                   10                  15

Phe Leu Arg Val
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic Construct

<400> SEQUENCE: 10

Val Arg Gln Lys Ser Asp Lys Glu Tyr Glu Arg Val Leu Gly Leu Gly
1               5                   10                  15

Leu Arg Arg Leu
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Construct

<400> SEQUENCE: 11

Ser Trp Leu Asn Gly Ser Gly Gly Val Val Leu Trp Leu Phe Ser Asn
1               5                   10                  15

Phe Cys Cys Gly
            20

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

Gly Ser Ser His Asn Asp Leu Arg Val Arg Arg Leu Thr
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

Glu Thr Glu Thr Phe His Pro Ile Thr Arg His Leu Ile Val Pro
1               5                   10                  15

<210> SEQ ID NO 14
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 14

Arg Met Pro Gln Trp Trp Gln Trp Met
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

His Pro Arg Arg Gln Pro Lys Arg Pro Ile
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

Thr His Gly Gly Arg His Pro
1               5

<210> SEQ ID NO 17
<211> LENGTH: 20
<212> TYPE: PRT
<213> ORGANISM: Artificial Sequence
<220> FEATURE:
<223> OTHER INFORMATION: Synthetic Construct

<400> SEQUENCE: 17

Ser Tyr Asn Thr Ile Lys Tyr His Glu Thr His Gly Gly Arg His Pro
1               5                   10                  15

Arg Arg Gln Pro
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic Construct

<400> SEQUENCE: 18

Asn Ala Ser Ser His Asn Asp Leu Arg Val Arg Arg Leu Thr Leu Ile
1               5                   10                  15

Ser Arg Leu Cys
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic Construct
```

```
<400> SEQUENCE: 19

Asn Gly Ser Ser His Asn Ala Leu Arg Val Arg Arg Leu Thr Leu Ile
1               5                   10                  15

Ser Arg Leu Cys
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic Construct

<400> SEQUENCE: 20

Asn Gly Ser Ser His Asn Asp Ala Arg Val Arg Arg Leu Thr Leu Ile
1               5                   10                  15

Ser Arg Leu Cys
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic Construct

<400> SEQUENCE: 21

Asn Gly Ser Ser His Asn Asp Leu Arg Ala Arg Arg Leu Thr Leu Ile
1               5                   10                  15

Ser Arg Leu Cys
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic Construct

<400> SEQUENCE: 22

Asn Gly Ser Ser His Asn Asp Leu Arg Val Arg Ala Leu Thr Leu Ile
1               5                   10                  15

Ser Arg Leu Cys
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic Construct

<400> SEQUENCE: 23

Asn Gly Ser Ser His Asn Asp Leu Arg Val Arg Arg Leu Ala Leu Ile
1               5                   10                  15

Ser Arg Leu Cys
            20

<210> SEQ ID NO 24
<211> LENGTH: 13
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 24

Xaa Ser Ser His Xaa Asp Ala Xaa Xaa Xaa Arg Xaa Thr
1               5                   10

<210> SEQ ID NO 25
<211> LENGTH: 40
<212> TYPE: PRT
<213> ORGANISM: Saccharomyces cerevisiae

<400> SEQUENCE: 25

Thr Ala Val Leu Glu Tyr Leu Thr Ala Glu Val Leu Glu Leu Ala Gly
1               5                   10                  15

Asn Ala Ala Lys Asp Leu Lys Val Lys Arg Ile Thr Pro Arg His Leu
            20                  25                  30

Gln Leu Ala Ile Arg Gly Asp Asp
        35                  40

<210> SEQ ID NO 26
<211> LENGTH: 40
<212> TYPE: PRT
<213> ORGANISM: Homo sapiens

<400> SEQUENCE: 26

Ala Ala Ile Leu Glu Tyr Leu Thr Ala Glu Val Leu Glu Leu Ala Gly
1               5                   10                  15

Asn Ala Ser Lys Asp Leu Lys Val Lys Arg Ile Thr Pro Arg His Leu
            20                  25                  30

Gln Leu Ala Ile Arg Gly Asp Glu
        35                  40

<210> SEQ ID NO 27
<211> LENGTH: 40
<212> TYPE: PRT
<213> ORGANISM: Mus musculus

<400> SEQUENCE: 27

Ala Ala Ile Leu Glu Tyr Leu Thr Ala Glu Val Leu Glu Leu Ala Gly
1               5                   10                  15

Asn Ala Ser Lys Asp Leu Lys Val Lys Arg Ile Thr Pro Arg His Leu
            20                  25                  30

Gln Leu Ala Ile Arg Gly Asp Glu
        35                  40

<210> SEQ ID NO 28
<211> LENGTH: 40
<212> TYPE: PRT
<213> ORGANISM: Drosophila melanogaster
```

```
<400> SEQUENCE: 28

Ala Ala Ile Leu Glu Tyr Leu Thr Ala Glu Val Leu Glu Leu Ala Gly
1               5                   10                  15

Asn Ala Ser Lys Asp Leu Lys Val Lys Arg Ile Thr Pro Arg His Leu
            20                  25                  30

Gln Leu Ala Ile Arg Gly Asp Glu
        35                  40

<210> SEQ ID NO 29
<211> LENGTH: 14
<212> TYPE: PRT
<213> ORGANISM: Artificial Sequence
<220> FEATURE:
<223> OTHER INFORMATION: Synthetic Construct

<400> SEQUENCE: 29

Arg Met Pro Gln Trp Trp Gln Trp Met Trp Val Arg Ala Lys
1               5                   10

<210> SEQ ID NO 30
<211> LENGTH: 30
<212> TYPE: PRT
<213> ORGANISM: Saccharomyces cerevisiae

<400> SEQUENCE: 30

Lys Met Ile Leu Tyr Asp Leu Cys Asp Asn Val Thr Thr Gln Trp Arg
1               5                   10                  15

Glu Trp Met Phe Pro His Asn Glu Thr Leu Pro Ala Leu Gly
            20                  25                  30

<210> SEQ ID NO 31
<211> LENGTH: 25
<212> TYPE: PRT
<213> ORGANISM: Saccharomyces cerevisiae

<400> SEQUENCE: 31

Val Leu Thr Gly Lys Lys Ile Pro Arg Trp Ser Asn Trp Cys Trp Leu
1               5                   10                  15

Phe Gly Leu Leu Ser Gly Leu Ala Met
            20                  25

<210> SEQ ID NO 32
<211> LENGTH: 27
<212> TYPE: PRT
<213> ORGANISM: Saccharomyces cerevisiae

<400> SEQUENCE: 32

Phe Gln Asp Leu Asn Lys Trp Tyr His Glu Lys Met Pro Lys Trp Ser
1               5                   10                  15

Gln Trp Val Ala Lys Gly Ser Ala Ala Tyr Leu
            20                  25

<210> SEQ ID NO 33
<211> LENGTH: 26
<212> TYPE: PRT
<213> ORGANISM: Saccharomyces cerevisiae

<400> SEQUENCE: 33

Leu Thr Glu Phe Glu Lys Arg Asn Pro Gln Trp Trp Lys Val Thr Leu
1               5                   10                  15

Arg Ser Phe Gly Gly Leu Leu Ile Ala Phe
            20                  25
```

```
<210> SEQ ID NO 34
<211> LENGTH: 13
<212> TYPE: PRT
<213> ORGANISM: Artificial Sequence
<220> FEATURE:
<223> OTHER INFORMATION: Synthetic construct

<400> SEQUENCE: 34

Gly Ser Ser His Asn Asp Ala Arg Val Arg Arg Leu Thr
1               5                   10

<210> SEQ ID NO 35
<211> LENGTH: 4
<212> TYPE: PRT
<213> ORGANISM: Artificial Sequence
<220> FEATURE:
<223> OTHER INFORMATION: Synthetic construct

<400> SEQUENCE: 35

Ser Lys Trp Thr
1

<210> SEQ ID NO 36
<211> LENGTH: 4
<212> TYPE: PRT
<213> ORGANISM: Artificial Sequence
<220> FEATURE:
<223> OTHER INFORMATION: Synthetic construct

<400> SEQUENCE: 36

Met Cys Met Ser
1

<210> SEQ ID NO 37
<211> LENGTH: 10
<212> TYPE: PRT
<213> ORGANISM: Artificial Sequence
<220> FEATURE:
<223> OTHER INFORMATION: Synthetic construct

<400> SEQUENCE: 37

Ser Lys Trp Thr Trp Arg Met Cys Met Ser
1               5                   10

<210> SEQ ID NO 38
<211> LENGTH: 3
<212> TYPE: PRT
<213> ORGANISM: Artificial Sequence
<220> FEATURE:
<223> OTHER INFORMATION: Synthetic construct

<400> SEQUENCE: 38

Pro Arg Pro
1

<210> SEQ ID NO 39
<211> LENGTH: 3
<212> TYPE: PRT
<213> ORGANISM: Artificial Sequence
<220> FEATURE:
<223> OTHER INFORMATION: Synthetic construct

<400> SEQUENCE: 39

Pro Pro Leu
1
```

```
<210> SEQ ID NO 40
<211> LENGTH: 8
<212> TYPE: PRT
<213> ORGANISM: Artificial Sequence
<220> FEATURE:
<223> OTHER INFORMATION: Synthetic construct

<400> SEQUENCE: 40

Pro Arg Pro Trp Gly Pro Pro Leu
1               5

<210> SEQ ID NO 41
<211> LENGTH: 19
<212> TYPE: PRT
<213> ORGANISM: Artificial Sequence
<220> FEATURE:
<223> OTHER INFORMATION: Synthetic construct

<400> SEQUENCE: 41

Val Arg Gln Lys Ser Asp Lys Glu Tyr Glu Arg Val Leu Gly Leu Gly
1               5                   10                  15

Leu Arg Arg
```